United States Patent
Arditi et al.

(10) Patent No.: US 8,491,482 B2
(45) Date of Patent: Jul. 23, 2013

(54) BLOOD FLOW ESTIMATES THROUGH REPLENISHMENT CURVE FITTING IN ULTRASOUND CONTRAST IMAGING

(75) Inventors: Marcel Arditi, Geneva (CH); Peter Frinking, Geneva (CH); Ilaria Gori, Genoa (IT)

(73) Assignee: Bracco Suisse S.A., Manno (CH)

( * ) Notice: Subject to any disclaimer, the term of this patent is extended or adjusted under 35 U.S.C. 154(b) by 1385 days.

(21) Appl. No.: 11/302,415

(22) Filed: Dec. 12, 2005

(65) Prior Publication Data

US 2006/0161062 A1    Jul. 20, 2006

Related U.S. Application Data

(63) Continuation-in-part of application No. PCT/EP2004/051090, filed on Jun. 11, 2004.

(30) Foreign Application Priority Data

Jun. 12, 2003 (EP) .................. 03405423
Dec. 17, 2003 (EP) .................. 03405903

(51) Int. Cl.
*A61B 8/14*     (2006.01)
*G01N 33/48*    (2006.01)
*G06F 17/10*    (2006.01)
*G06F 7/48*     (2006.01)
*G06K 9/00*     (2006.01)

(52) U.S. Cl.
USPC .............. 600/458; 702/19; 703/2; 703/11; 382/128

(58) Field of Classification Search
None
See application file for complete search history.

(56) References Cited

U.S. PATENT DOCUMENTS 5,860,931 A    1/1999   Chandler
6,080,107 A    6/2000   Poland
(Continued)

FOREIGN PATENT DOCUMENTS

EP    0458745    11/1991
EP    0554213    4/1993
(Continued)

OTHER PUBLICATIONS

Wei K. et al., "Quantification of Myocardial Blood Flow With Ultrasound-Induced Destruction of Microbubbles Administered as a Constant Venous Infusion", Circulation, American Heart Association, Dallas, TX, US., vol. 5, No. 97; Feb. 10, 1998, pp. 473-483.

(Continued)

*Primary Examiner* — Long V. Le
*Assistant Examiner* — Angela M Hoffa
(74) *Attorney, Agent, or Firm* — Bryan A. Santarelli; Graybeal Jackson LLP

(57) ABSTRACT

Method and system for non-invasive quantification of tissue perfusion obtainable by a destruction-reperfusion process that provide a signal representative of local agent concentration during reperfusion, by deriving at least one local tissue perfusion value. The system is configured to adjust or relate function of time with S-shape characteristics to the signal proportional to the local agent concentration during reperfusion, and making a correspondence between at least one value of at least one parameter of the function with S-shape characteristics with at least one local tissue perfusion value (such as mean velocity, mean transit time, mean flow, perfusion volume) or attribute (such as the blood flow pattern, flow distribution variance or skewness).

47 Claims, 23 Drawing Sheets

U.S. PATENT DOCUMENTS

| | | | | |
|---|---|---|---|---|
| 6,149,597 | A * | 11/2000 | Kamiyama | 600/458 |
| 6,315,730 | B1 | 11/2001 | Hoff et al. | |
| 6,461,303 | B2 * | 10/2002 | Angelsen | 600/458 |
| 6,547,738 | B2 * | 4/2003 | Lysyansky | 600/458 |
| 7,054,454 | B2 | 5/2006 | Causevic et al. | |
| 7,415,142 | B2 * | 8/2008 | Breeuwer | 382/128 |
| 7,753,850 | B2 * | 7/2010 | Averkiou et al. | 600/458 |
| 8,021,303 | B2 * | 9/2011 | Frinking et al. | 600/458 |
| 2002/0029130 | A1 * | 3/2002 | Eryurek et al. | 702/183 |
| 2002/0040189 | A1 | 4/2002 | Averkiou et al. | |
| 2003/0092991 | A1 | 5/2003 | Sehgal | |
| 2003/0114759 | A1 | 6/2003 | Skyba et al. | |
| 2003/0185408 | A1 * | 10/2003 | Causevic et al. | 381/94.1 |
| 2008/0228080 | A1 | 9/2008 | Arditi et al. | |
| 2008/0294027 | A1 | 11/2008 | Frinking et al. | |

FOREIGN PATENT DOCUMENTS

| | | |
|---|---|---|
| WO | 9115244 | 10/1991 |
| WO | 9409829 | 5/1994 |
| WO | 9516467 | 6/1995 |
| WO | WO 02/056666 A2 | 7/2002 |
| WO | 02102251 | 12/2002 |
| WO | 2006067201 | 6/2006 |
| WO | 2006067203 | 6/2006 |

OTHER PUBLICATIONS

David Cosgrove, Robert Eckersley, "Quantification of Blood Flow", European Radiology, vol. 11, No. 8, 2001, pp. 1338-1344.

International Search Report for PCT/EP2004/051090 dated Oct. 1, 2004.

International Search Report for International Patent Application Serial No. PCT/EP2005/057065; European Patent Office, Oct. 25, 2006.

International Search Report for International Patent Application Serial No. PCT/EP2005/057068; European Patent Office, Mar. 20, 2006.

Byrd, Richard H., Schnabel, Robert B., Schultz, Gerald A., "Approximate Solution of the Trust Region Problem by Minimization Over Two-Dimensional Subspaces", University of Colorado at Boulder, Department of Science.

Coleman, Thomas F., Li, Yuying, "An Interior Trust Region Approach for Nonlinear Minimization Subject to Bounds"; Siam J. Optimization, Society for Industrial and Applied Mathematics; vol. 6, No. 2, pp. 418-445, May 1996.

Coleman, Thomas F., Li, Yuying, "On the convergence of Interior-reflective Newton Methods for Nonlinear Minimization Subject to Bounds"; The Mathematical Programming Society, Inc. 1994 p. 189-224.

Wei, Kevin, "Detection and Quantification of Coronary Stenosis Severity with Myocardial Contrast Echocardiography" Progress in Cardiovascular Diseases, vol. 44, No. 2, Sep. 10, 2001; p. 81-100.

Wei, Kevin, Le, Elizabeth, Bin, Jian-Ping, Coggins, Matthew, Thorpe, Jerrel, Kaul, Sanjiv, "Quantification of Renal Blood Flow with Contrast-Enhanced Ultrasound"; Journal of the American College of Cardiology; vol. 37 No. 4 2001; p. 1135-1140.

Kharchakdjian, Raffi, Burns, Peter N., Henkelman, Mark; "Fractal Modeling of Microbubble Destruction-reperfusion in Unresolved Vessels"; 2001 IEEE Ultrasonics Symposium p. 1669-1673.

Rim, Se-Joong, Poi-Leong, Howard, Lindner, Jonathan R., Couture, Daniel, Ellegala, Dilantha, Mason, Holland, Durieux, Marcel, Kassel, Neal F., Kaul, Sanjiv; "Quantification of Cerebral Perfusion with "Real-Time" Contrast-Enhanced Ultrasound"; Journal of the American Heart Association Circulation 2001; 104;p. 2582-2581.

Schlosser, Thomas, Pohl, Christoph, Veltmann, Christian, Lohmaier, Stefan, Goenechea, Jon, Ehlgen, Alexander, Koster, Jorg, Bimmel, Dieter, Kuntz-Hehner, Stefanie, Becher, Harald, Tiemann, Klaus; "Feasibility of the Flash-Replenishment Concept in Renal Tissue: Which Parameters Affect the Assessment of the Contrast Replenishment"; Ultrasound in Med & Biol., vol. 27, No. 7,p. 937-944 2001.

Murthy, Thippeswamy H., Li, Peng, Locvicchio, Elizabeth, Baish, Cheryl, Dairywala, Ismail, Armstrong, William F., Vannan, Mani; "Real-Time Myocardial Blood Flow Imaging in Normal Human Beings with the Use of Myocardial Contrast Echocardiography"; American Society of Echocardiography, 2001, p. 698-705.

Kinsler, Lawrence E., Frey, Austin R., Coppens, Alan B., Sanders, James V.; Fundamentals of Acoustics; John Wiley & Sons Third Edition; p. 172-174.

Gautschi, Walter; Handbook of Mathematical Functions; Dover Publications, Inc. New York; p. 295-297.

Veltmann, Christian, Lohmaier, Stefan, Schlosser, Thomas, Shai, Sonu, Ehlgen, Alexander, Pohl, Christoph, Becher, Harald, Tiemann, Klaus; "On the Design of a Capillary Flow Phantom for the Evaluation of Ultrasound Contrast Agents at Very Low Flow Velocitied", Ultrasound in Med. & Biol., vol. 28, No. 5, p. 625-634 2002.

Scabia, Marco, Biagi, Elena, Masotti, Leonardo; "Hardware and Software Platform for Real-Time Processing and Visualization of Echographic Radiofrequency Signals"; IEEE Transactions on Ultrasonics, Ferroelectrics, and Frequency Control, vol. 49, No. 10, Oct. 2002 p. 1444-1452.

Qian, Hong, Bassingthwaighte, James B.; "A Class of Flow Bifurcation Models with Lognormal Distribution and Fractal Dispersion"; J. theor. Biol. Academic Press (2000) p. 205, 261-268.

Krix, Martin, Plathow, Christian, Kiessling, Fabian, Herth, Felix, Karcher, Andreas, Essig, Marco, Schmitteckert, Harry, Kauczor, Hans-Ulrich, Delorme, Stefan; "Quantification of Perfusion of Liver Tissue and Metastases Using a Multivessel Model for Replenishment Kinetics of Ultrasound Contrast Agents"; Ultrasound in Med. & Biol., vol. 30, No. 10 p. 1355-1363, 2004.

Lucidarme, Olivier, Franchi-Abella, Stephanie, Correas, Jean-Michel, Bridal, S. Lori; Kurtisovski, Erol, Berger, Genevieve; "Blood Flow Quantification with Contrast-enhanced US: Entrance in the Section" Phenomenon-Phantom and Rabbit Study; Experimental Blood Flow Quantification: "Entrance in the Section" Phenomenon; Radiology; 2003; vol. 228 No. 2, 473-479.

Eyding, Jens, Wilkening, Wilko, Dipl-Ing, Reckhardt, Markus , Schmid, Gebhard, Meves, Saskia, Ermert, Helmut, Przuntek, Horst, Postert, Thomas; "Contrast Burst Depletion Imaging (CODIM) A New Imaging Procedure and Analysis Method for Semiquantitative Ultrasonic Perfusion Imaging"; STROKE, vol. 34, Jan. 2003 p. 77-83; XP002354455.

* cited by examiner

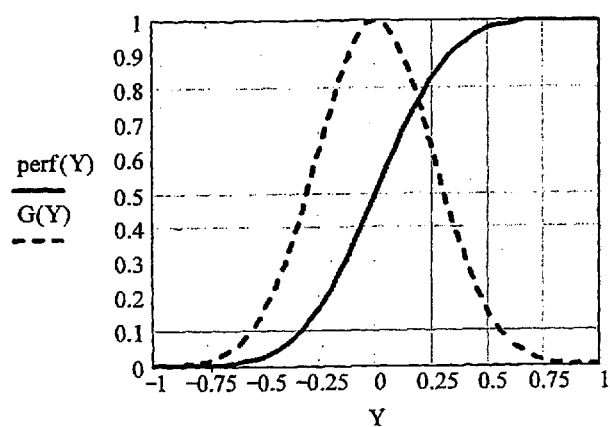
Fig. 2
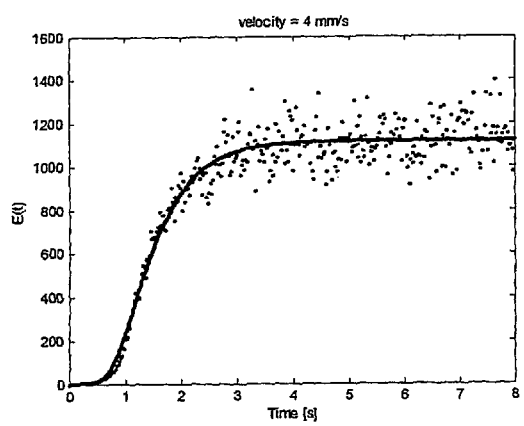 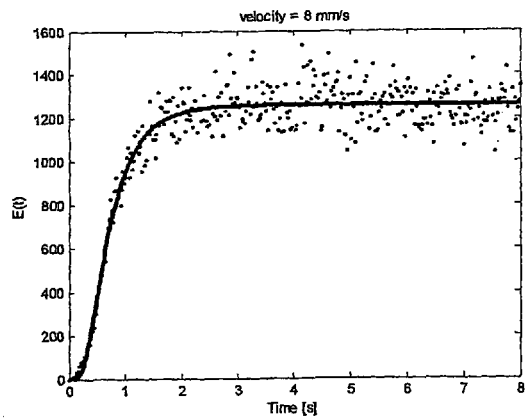
Fig. 3a  Fig. 3b

μ = 1.25    σ² = 0.5    γ = 1.88

μ = 1.25    σ² = 0.02    γ = 0.34

μ = 1.25    σ² = 0.5    γ = 1.88

μ = 1.25    σ² = 0.02    γ = 0.34

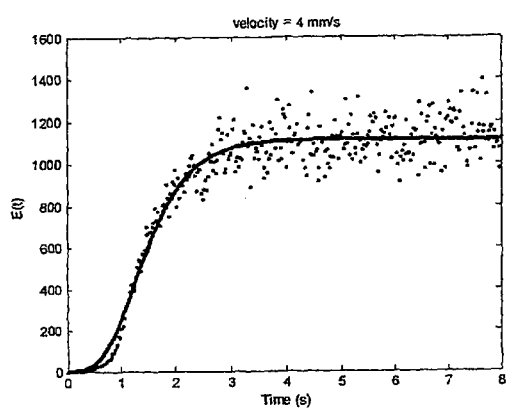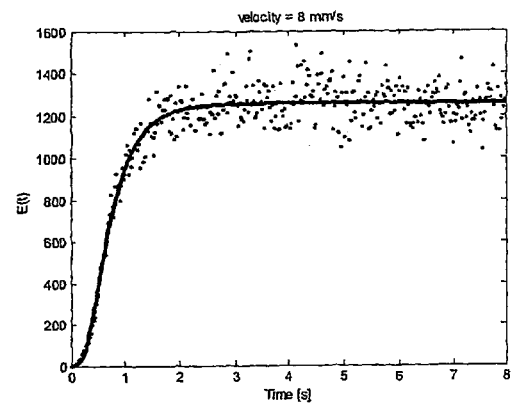
Fig. 7a  Fig. 7b
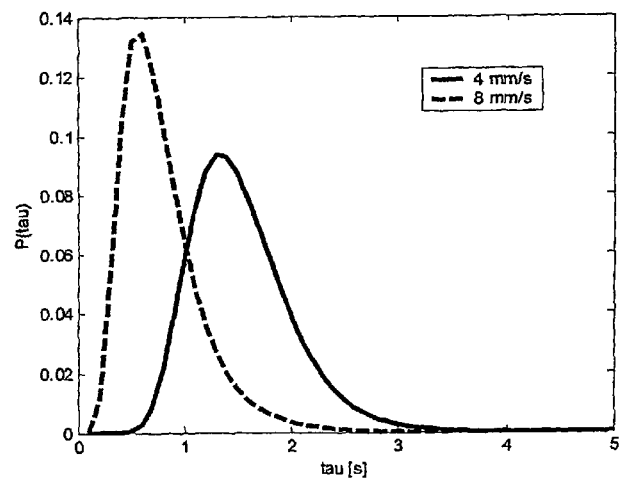
Fig. 8

BLOOD FLOW ESTIMATES THROUGH REPLENISHMENT CURVE FITTING IN ULTRASOUND CONTRAST IMAGING

PRIORITY CLAIM

This is a continuation-in-part application which claims priority from PCT/EP2004/051090, published in English, filed Jun. 11, 2004, which claims priority from European patent Application No. 03405423.9, filed Jun. 12, 2003 and European patent Application No. 03405903.0, filed Dec. 17, 2003, which are incorporated herein by reference.

TECHNICAL FIELD

This invention relates to a blood-flow estimation technique in a process involving the destruction/replenishment monitoring of gas-filled microvesicles, where flow parameters are derived from an analysis of the replenishment kinetics. More specifically, the invention concerns a method of non-invasive quantification of perfusion in a tissue of a live subject. The invention further relates to a computer program for performing the method, and to a product embodying the program. Moreover, the invention also concerns a corresponding system for non-invasive quantification of perfusion, and an apparatus for use in this system.

BACKGROUND

Use of suspensions of gas bubbles in a carrier liquid, as efficient ultrasound reflectors is well known in the art. The development of these suspensions as means for enhancement of ultrasound imaging followed early observations that rapid intravenous injections of aqueous solutions can cause dissolved gases to come out of solution by forming bubbles. Due to their substantial difference in acoustic impedance relative to blood, these intravascular gas bubbles were found to be excellent reflectors of ultrasound. The injection of suspensions of gas bubbles in a carrier liquid into the blood stream of a living organism strongly reinforces ultrasonic echography imaging, thus enhancing the visualization of internal organs. Since imaging of organs and deep seated tissues can be crucial in establishing medical diagnosis, a lot of effort has been devoted to the development of stable suspensions of highly concentrated gas bubbles which at the same time would be simple to prepare and administer, would contain a minimum of inactive species and would be capable of long storage and simple distribution.

The simple dispersion of free gas bubbles in an aqueous medium is however of limited practical interest, since these bubbles are in general not stable enough to be useful as ultrasound contrast agents.

Interest has accordingly been shown in methods of stabilizing gas bubbles for echography and other ultrasonic studies, for example using emulsifiers, oils, thickeners or sugars, or by entraining or encapsulating the gas or a precursor thereof in a variety of systems. These stabilized gas bubbles are generally referred to in the art as "microvesicles", and may be divided into two main categories. A first category of stabilized bubbles or microvesicles is generally referred to in the art as "microbubbles" and includes aqueous suspensions in which the bubbles of gas are bounded at the gas/liquid interface by a very thin envelope involving a surfactant (i.e. an amphiphilic material). A second category of microvesicles is generally referred to in the art as "microballoons" or "microcapsules" and includes suspensions in which the bubbles of gas are surrounded by a solid material envelope formed of natural or synthetic polymers. Another kind of ultrasound contrast agent includes suspensions of porous microparticles of polymers or other solids, which carry gas bubbles entrapped within the pores of the microparticles.

The present invention is particularly concerned with, although not limited to, the use of an ultrasound contrast agent (UCA) including an aqueous suspension of gas microbubbles, for exploiting a technique comprising the perfusion, destruction and monitoring of the replenishment of said UCA. Gas-filled microballoons may conveniently also be used for the present technique.

Microbubbles are typically defined as gas-filled microvesicles stabilized essentially by a layer of amphiphilic material. Aqueous suspensions of microbubbles are typically prepared by contacting powdered amphiphilic materials, e.g. freeze-dried preformed liposomes or freeze-dried or spray-dried phospholipid solutions, with air or other gas and then with aqueous carrier, and agitating to generate a microbubble suspension which must then be administered shortly after its preparation.

Examples of suitable aqueous suspensions of gas-filled microvesicles, in particular microbubbles and microballoons, and of the preparation thereof are disclosed, for instance, in the following patent applications: EP 0458745, WO 91/15244, EP 0554213, WO 94/09829 and WO 95/16467.

In 1998, investigators proposed to monitor the replenishment rate of a microbubble-based Ultrasound Contrast Agent (UCA), following destruction from an imaging plane by the ultrasound imaging instrument (Wei, K., Jayaweera, A. R., Firoozan, S., Linka, A., Skyba, D. M., and Kaul, S., "Quantification of Myocardial Blood Flow With Ultrasound-Induced Destruction of Microbubbles Administered as a Constant Venous Infusion," *Circulation*, vol. 97 1998.). This possibility of destroying microbubbles locally essentially serves the purpose of providing a so-called "negative-bolus" of agent to the image plane, in an organ otherwise under an essentially constant perfusion of agent during the time of the measurement. Observation of the rate of reperfusion of UCA in the image plane, under continuous (i.e. so-called "real-time") or intermittent (i.e. triggered) imaging, allowed an estimate of the organ perfusion, i.e. of the local flow-parameters.

This technique has been widely adopted. Extensive published literature has consistently reported using an optimal fit of the replenishment video or Doppler signal as a function of time, with an expression describing the dilution kinetics of an indicator in a single-compartment volume (in the form of a growing monoexponential function). See for example the following publications:

K. Wei, Detection and Quantification of Coronary Stenosis Severity With Myocardial Contrast Echocardiography, *Progress in Cardiovascular Diseases,* 44(2), 2001, 81-100: FIG. 8 of this reference shows a video intensity versus pulsing interval relation fitted to a monoexponential function.

Kevin Wei, Elizabeth Le, Jian-Ping Bin, Matthew Coggins, Jerrel Thorpe, Sanjiv Kaul. Quantification of Renal Blood Flow With Contrast-Enhanced Ultrasound. *J. Am Coll Cardiol,* 2001; 37:1135-40: FIG. 2 of this reference shows the monoexponential relationship of video intensity versus pulsing interval(s).

Kharchakdjian, R., Burns, P. N., and Henkelman, M. Fractal Modeling of Microbubble Destruction-Reperfusion in Unresolved Vessels. *IEEE Ultrasonics Symposium,* 2001: This paper discusses the different types of reperfusion concentration-vs-time curves for different physiological flow conditions.

Rim, S.-J., Leong-Poi, H., Lindner, J. R, Couture, D., Ellegala, D., Masson, H. Durieux, M, Kasse, N. F. and Kaul S., Quantification of Cerebral Perfusion with Real-Time Contrast-Enhanced Ultrasound, *Circulation*, vol. 104, 2001, 2582-2587: FIGS. 2 and 3 of this reference show plots of acoustic intensity versus time, fitted by monoexponential functions, while the data recorded is described as proportional to agent concentration.

Schlosser et al, Feasibility of the Flash-Replenishment Concept in Renal Tissue: Which Parameters Affect the Assessment of the Contrast Replenishment?, Ultrasound in Med. & Biol., Vol. 27, pp 937-944, 2001: this article analyses contrast agent replenishment and also applies the nonlinear curve fitting using the monoexponential function introduced by Wei et al.

Murthy T H, Li P, Locvicchio E, Baisch C, Dairywala I, Armstrong W F, Vannan M. Real-Time Myocardial Blood Flow Imaging in Normal Human Beings with the use of Myocardial Contrast Echocardiography. *J Am Soc Echocardiogr*, 2001, 14(7):698-705: FIG. 7 of this reference shows that the video intensity versus time curve is fitted with the "1-phase exponential association equation".

WO 02/102251 describes microbubble destruction/replenishment and shows in its FIG. 2b the monoexponential function of microvascular video intensity versus time, from which microvascular flow intensity is described as represented by the tangent to the initial slope of the monoexponential function. Its FIG. 2c shows the monoexponential function of video intensity versus pulsing interval (Intermittent mode).

The present inventors have observed that the prior heuristic approaches gave encouraging results because the echo signals in all echo-imaging instruments undergo heavy nonlinear compression (also called log-compression), before they are made available to the observer in the form of a video signal. Fitting the video data with the monoexponential function thus allowed to produce flow-estimates related to the actual local organ perfusion, which so far have been judged satisfactory.

The present inventors have however observed that the known approach is very sensitive to the user-selected instrument settings, such as receiver gain, log-compression, and so on. The parameters extracted are also specific to each instrument type, and thus cannot be compared between investigators using different equipment or settings. Furthermore, the perfusion parameters extracted from the state-of-the-art technique are only relative estimates, and are not suitable for an absolute quantitative evaluation of the flow parameters.

SUMMARY

This invention is motivated by the fact that the expression derived from the indicator-dilution theory (the so-called "monoexponential function) does not describe in the correct way the kinetics of UCA reperfusion following destruction in an image-plane, or tomographic slice.

This invention addresses the above-indicated problem by providing a new approach, allowing flow parameter estimates that are essentially user- and instrument-independent, as well as having a physical meaning in absolute physical terms.

In one aspect, the invention provides a method of non-invasive quantification of perfusion in a tissue of a live subject. The method starts with the step of providing a sequence of echo signals, which are indicative of a replenishment of an imaging contrast agent in the tissue. A parametric S-shape function of time is associated (i.e., adjusted or related) with the echo signals. A correspondence is then made between at least one value of one or more parameters of the S-shape function and at least one local tissue perfusion value (such as mean velocity, mean flow, perfusion volume) or attribute (such as blood flow pattern).

An S-shape function or a function with S-shape characteristics as defined in the present description and claims is a mathematical function including an initial portion with a substantially constant initial value, a final portion with a substantially constant final value, and a central portion between the initial portion and the final portion wherein said S-shape function changes monotonically from the initial value to the final value. Preferably, said function has at least one zero second derivative in the central portion thereof. Furthermore, said S-shape function has preferably essentially zero first derivatives in said initial portion and final portion thereof. Examples of S-shape functions are the "error function", the hyperbolic tangent, the sigmoid function, the cumulative normal distribution function, the cumulative lognormal distribution function or any polynomial approximation thereof.

In an embodiment of the invention, said contrast agent includes microvesicles that have the capacity to reflect acoustic energy. The step of providing the sequence of echo signals includes applying an ultrasound pulse in an imaging plane of an ultrasound imaging apparatus; the ultrasound pulse is applied at an acoustic pressure sufficiently high to result in the destruction of a significant portion of the microvesicles present within that plane. A sequence of further ultrasound pulses is then applied in said imaging plane; the further ultrasound pulses have an acoustic pressure sufficiently low to preserve a major portion of the microvesicles. The step of applying the sequence of further ultrasound pulses is repeated at predetermined subsequent instants; the echo signals originating from said plane by the further ultrasound pulses are then recorded, in order to monitor the replenishment of microvesicles within the imaging plane at said subsequent instants.

As a further enhancement, said echo signals are processed before associating the S-shape function. Particularly, the echo signals are made proportional to a local concentration of the microvesicles; in this way, processed echo signals are produced that are in proportion to a concentration of the contrast agent at any location within the imaging plane. On the basis of the ultrasound beam geometry and the extent of UCA destruction, the invention in one embodiment relates the average flow velocity across the imaging plane to the time needed to reach one half of the steady-state UCA concentration, as determined by a best-fit of the aforementioned S-shape function. Preferably, the S-shape perfusion function is fitted on echo signals generated by the UCA, the instantaneous amplitude of which has been made proportional to the local concentration of UCA having generated these echo signals. This proportionality is typically obtained by suitably linearizing the final data obtained from the ultrasound analysis, which are generally of two types. A first type of data are referred to as "images" and include echo signals displayed as analog or digital video signals, or any other grayscale or colorized amplitude 2-dimensional maps (2D-maps), which are obtained by a process including non-linear dynamic range compression (e.g. logarithmic compression) of the generated echo signals. Images are typically associated with image elements (pixels) having a predetermined amplitude. A second type of data are referred to as "raw" echo signals and include signals with an amplitude proportional to the ultrasound echo amplitude, typically the radio-frequency (rf) echo signals which are directly obtained from the ultrasound apparatus.

The terms "linearization" or "linearized signal" as used herein apply to an ultrasound echo signal processed in a way that makes its amplitude in direct proportion to the local UCA microvesicle concentration that produced it. This reflects the nature of the scattering of acoustic energy by a population of randomly spaced scatterers, which results in an echo signal power proportional to UCA concentration. When dealing with rf or demodulated rf signals proportional to acoustic pressure amplitude, such linearization can be obtained by appropriate squaring of the raw echo signal amplitude, whereas when dealing with log-compressed images, such linearization can be obtained by appropriate inverse log-compression and squaring of the amplitude values of each pixel, thus obtaining a proportionality between amplitude of the processed signal and UCA concentration.

Alternatively, the S-shape function can also be fitted on the "non-linearized" echo data (e.g. images), i.e. data which are not proportional to the local UCA concentration. In this case, the selected S-shaped function to be fitted on the non-linearized data is modified by the same process as the one causing the nonlinearity between UCA concentration and echo data (e.g. square-root and log-compression of the S-shaped functions).

The echo signals on which the curve fitting is performed are typically obtained by applying a sequence of ultrasound pulses in an imaging plane of the ultrasound apparatus and the replenishment of microvesicles within the imaging plane is monitored by recording (as a function of time) the amplitudes of said ultrasound echo signals originating from the microvesicles comprised in said plane.

One embodiment for providing a sequence of echo signals, which are indicative of a replenishment of an imaging contrast agent in the tissue, may comprise the following step:

provide a constant supply of UCA to an organ or region of interest, or inject the UCA as a bolus in conditions allowing a sufficiently constant UCA perfusion during the few seconds required by the destruction-replenishment methods;

record the echo signals in the region of interest, immediately before the application of a UCA destruction frame, at an acoustic energy level below a predetermined threshold capable of destroying said microvesicles;

apply said UCA destruction frame by means of an ultrasound pulse in the imaging plane of an ultrasound imaging apparatus having an acoustic energy higher than said predetermined threshold and sufficient to cause the destruction of a significant portion of the microvesicles present within that plane;

record the echo signals in the region of interest immediately following the application of said UCA destruction frame, at an acoustic energy level below said predetermined microvesicle-destruction threshold.

The following step can be performed on any sequence of echo signals which are indicative of a replenishment of an imaging contrast agent in the tissue (such as those obtainable according to the above methodology), in order to determine the perfusion parameters of said tissue:

perform best-fit estimates of said signals to a S-shape function (e.g. of the family of the "error-function"), on a local basis, which can be either within user-chosen Areas Of Interest (AOI), at the local pixel-by-pixel level in order to allow the generation of parametric images of perfusion, or at the level of groups-of-pixels, as determined by the speckled nature of ultrasound images when obtained through the use of coherent beams;

make a correspondence between at least one value of at least one parameter of the function with S-shape characteristics and at least one local tissue perfusion value (such as mean transit time, mean velocity, mean flow, perfusion volume) or attribute (such as blood flow pattern, flow distribution variance or skewness).

Preferably, before performing the best-fit estimates, the echo signals are processed (e.g. linearized) to obtain processed signals which are proportional to the local UCA concentration, in order to perform said best-fit on data which are proportional to the UCA concentration.

As an example of correspondence between a value of a parameter of the function with S-shape characteristics and a local tissue perfusion value, the average flow-velocity can be estimated by computing the ratio of the half-thickness of the zone (or slice) destroyed by the destruction frames, divided by the mean transit time determined by the local parametric fits.

Another example is that the amplitude found as best-fit values may be interpreted, once calibrated, as a quantity proportional to blood volume in the analyzed region, and used to estimate flow values from the product of the amplitude and the flow velocity.

Yet another example is that the spread in the distribution of different flow contributions (such as variance and skewness) may also be found from best-fit values to modeled sum of individual perfusion functions.

These flow parameter estimates can be displayed either within the AOIs used, or as two-dimensional maps in the form of parametric images.

The S-shape functions obtained according to the methods described above can also be used to estimate a probability density distribution of transit times or velocities of the microvesicles during the reperfusion (for example, in the different capillaries).

For this purpose, in an embodiment of the invention the S-shape functions are analyzed by a wavelet decomposition method.

Preferably, the echo signal proportional to local concentration is differentiated twice before being analyzed by the wavelet decomposition method.

A suggested choice for defining a mother wavelet used for the decomposition consists of the second time derivative of a cumulative normal distribution function used to describe the S-shape function for a single flow value.

In a different embodiment, the echo signals are analyzed by a one step or multiple step process to estimate the distribution of contributions at different flow transit times or velocities.

Particularly, a first set of flow transit times or velocities are selected; a first estimate is then made by a best fit of a linear combination of a plurality of S-shaped functions with the echo signals.

In a preferred implementation, a second estimate is made to define a second set of flow transit times or velocities; in this case, the first estimate is used as a basis for defining said second set.

Still more preferably, the second estimate is used to provide an initial set of values for making a third estimate.

A suggested choice for the second estimate consists of using cubic spline extrapolation.

A way to further improve the solution is the use a neural network analysis to make the third estimate.

Typically, the neural network is defined by a plurality of weights (for the flow transit times or velocities) and a plurality of bias values (for the weighted flow transit times or velocities). The neural network is trained by iteratively adjusting the bias values and the weights; preferably, the bias values and each negative weight are periodically reset to zero.

In a preferred embodiment, the resetting is performed with a periodicity equal to a number of iterations between 50 and 100.

As a further enhancement, the first estimate is made using at most 16 and preferably at most 8 S-shaped functions.

Moreover, the second estimate can be made using a set of at least 8 and preferably at least 16 flow transit times or velocities.

A further aspect of the present invention provides a computer program for performing the above-described method.

A still further aspect of the invention provides a program product embodying this computer program.

Moreover, a different aspect of the invention provides a corresponding system for non-invasive quantification of perfusion in a tissue of a live subject.

Another aspect of the invention provides an apparatus for use in that system, such apparatus being provided with means for inputting said echo signals.

As will be demonstrated below:

(1) The parameters extracted from the S-shape function by the method according to the invention are independent of the equipment or settings used, and can be compared between investigators using different equipment or settings. Moreover these extracted parameters are suitable for absolute quantitative evaluation.

(2) The invention provides a simple quantification method for in-vivo blood flow parameters that works surprisingly well despite the great complexity of the actual organ perfusion. Estimates of a mean flow velocity along the perpendicular to the scan plane may be made even in the presence of superimposed flow contributions with different velocities and arising from different arbitrary directions.

(3) According to the present invention the curve fitting can be based on a parametric expression integrating the acoustic sensitivity properties of an ultrasound probe in the elevation direction, while respecting the correspondence between the power in the echo signal with the local microvesicle concentration. It is then sufficient to preserve these corresponding properties in any modification of the fitting function chosen. With this condition, and a knowledge of the width of the microvesicle-destruction zone in elevation, it is possible to estimate absolute blood flow parameters, as well as their statistical distributions (e.g. flow transit time or velocity).

BRIEF DESCRIPTION OF THE DRAWINGS

In the accompanying schematic drawings, which are given by way of example:

FIG. 2 is a graph showing the S-shape function of contrast agent signal power as it reperfuses a zone where it has been destroyed, such S-shape function being used in the method according to the invention;

FIGS. 3a and 3b are graphs showing experimentally recorded echo power functions following destruction, in an in vitro setup, fitted with cumulative lognormal distribution functions according to one embodiment of the invention;

FIGS. 7a and 7b are graphs showing experimentally recorded echo power functions following destruction, in an in-vitro setup, fitted according to yet another embodiment of the invention with sums of reperfusion functions according to an S-shape lognormal distribution of transit times;

FIG. 8 is a graph showing the lognormal transit time distributions found as optimal fits to the data of FIG. 7;

DETAILED DESCRIPTION

Figure 1A:
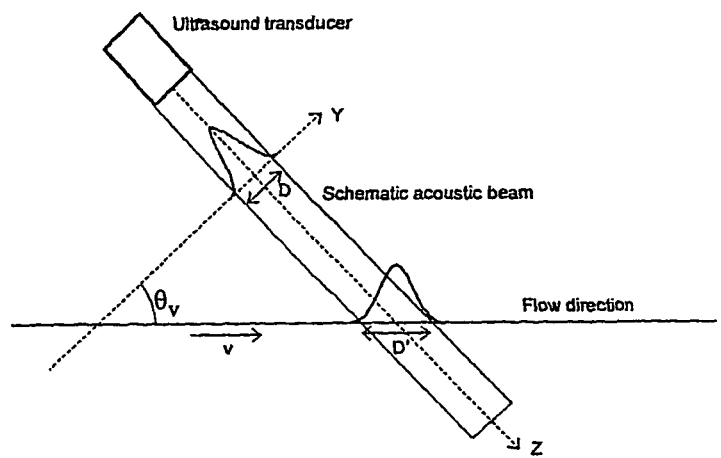
FIG. 1a is a diagram illustrating the projection of an acoustic beam from an ultrasound transducer.

In the following description, the symbols used are defined as follows:

| | |
|---|---|
| x | space coordinate within image plane, (lateral) direction orthogonal to beam |
| y | space coordinate across image plane, (elevation) direction orthogonal to beam |
| z | space coordinate within image plane, (depth) direction along the beam |
| D | spatial extent of microvesicle destruction, in elevation (y) direction |
| f | ultrasound frequency |
| c | speed of sound |
| $\lambda$ | ultrasound wavelength |
| m | mean of the natural logarithm |
| s | standard deviation of the natural logarithm |
| $\mu$ | mean of the lognormal distribution |
| $\sigma^2$ | variance of the lognormal distribution |
| $\gamma$ | skewness of the lognormal distribution |
| $\tau$ | flow transit time from edge to center of destroyed zone |
| $\tau_{mean}$ | mean of $\tau$ |
| C | probability density or relative concentration of microvesicles |
| A | amplitude factor in parametric equation |
| O | offset factor in parametric equation |
| a | half-aperture width in y direction |
| v | local flow velocity ($v_x$, $v_y$, $v_z$ components) |
| $K_{Tx}$, $K_{Rx}$ | $2a/\lambda z$ parameters on transmit and receive, respectively |

-continued

| | |
|---|---|
| K | transmit-receive parameter determined by $K^2 = K^2_{Tx} + K^2_{Rx}$ |
| Y | unitless variable $Y = K\,y$ |
| θ | angle between flow direction and normal to image plane |
| β | "velocity" term of the monoexponential function |
| GL | Gray level of a video signal |
| t | time |
| dt | time sample in wavelet analysis |
| η | deviation term in a cumulative lognormal probability distribution function |
| Γ | arbitrary proportionality constant |

The invention proposes a method of organ-perfusion quantification based on the study of the reperfusion kinetics of a microvesicle-based ultrasound contrast agent (UCA). This method requires administering the UCA, waiting for a certain time to establish a steady-state of UCA concentration in the organ or region of interest (typically between 5 and 30 seconds), applying one or more agent-destruction frames at sufficiently high acoustic pressure to destroy the UCA microvesicles in a slice comprising the imaging plane, and monitoring the reperfusion, or replenishment, kinetics. Reaching the required steady-state perfusion can be accomplished by either a continuous infusion of UCA, or a bolus in such a way as to reach a fairly constant infusion rate for several seconds (typically between 1 and 15 seconds).

Reperfusion Kinetics

The reperfusion kinetics is analyzed on the basis of a linearized signal proportional to local UCA concentration, i.e. a signal proportional to backscattered acoustic power. The perfusion parameters can then be deduced from the replenishment kinetics. Conventional ultrasound imaging, in either "B-mode" or "2D-Doppler", is a tomographic approach, where a slice of tissue is interrogated by rapid scanning of a focused acoustic beam. The spatial resolution in such imaging modes is primarily governed by the transmit-receive ultrasound sensitivity distributions at each depth in three dimensions: the lateral direction, defined as the direction across the acoustic beamwidth within the image plane; the axial direction, along the beam propagation direction within the image plane, and the elevation direction, in a direction perpendicular to the image plane.

The thickness of the slice where UCA microvesicles are destroyed by the application of sufficiently-high acoustic pressure is determined by the acoustic beamwidth in the elevation direction and by the actual acoustic level applied. During the replenishment phase, the UCA microvesicles re-enter the destroyed-slice volume and are detected by the echographic instrument according to its spatial sensitivity along the beam elevation direction. What the applicant has found is that the relationship between the observed echo-power as a function of time and the actual reperfusion kinetics is uniquely determined by the spatial transmit-receive distribution in the pulse-echo mode, along the elevation direction. Contrary to this, the generally accepted concept for this relationship has been borrowed from the indicator-dilution theory, which describes the time evolution of a concentration of an indicator as it is randomly diluted in a homogeneous medium (e.g. Wei, K., Jayaweera, A. R., Firoozan, S., Linka, A., Skyhu, D. M., and Kaul, S., "Quantification of Myocardial Blood Flow With Ultrasound-Induced Destruction of Microbubbles Administered as a Constant Venous Infusion," *Circulation*, vol. 97 1998). Prior investigators have been basing their approach mostly on the video intensity level observed during contrast replenishment, which is a quantity strongly determined by the so-called "log-compression" of the echographic instruments. This led to the choice of the mono-exponential function as a model of reperfusion kinetics, with a general form given as:

$$GL(t) = A(1 - e^{-\beta t}),$$

where A is the steady-state amplitude, β is a "velocity" term of the monoexponential function, and the time origin is taken at the instant immediately following the last UCA destruction pulses. In the prior art (e.g. the cited articles by Wei et al.), the values A, β and Aβ have commonly been interpreted as quantities proportional to "blood volume", "blood velocity" and "blood flow" within the analyzed region. However, this approach is not based on a function proportional to the local UCA concentration at a given time, and is plagued by a large sensitivity to user settings, such as gain, log-compression parameters, etc.

This invention discloses a simple quantification method that, despite the great complexity of the actual organ perfusion (microvasculature structure, random directions of flow, sum of different flow values, etc.), works surprisingly well in the in-vivo case.

The application of a UCA destruction frame by means of a pulse having sufficiently high acoustic intensity results in a deficit of UCA microvesicles in a volume determined, in elevation, by the ultrasound beam pressure-distribution and, laterally, by the extent of the area scanned by the ultrasound probe. The high acoustic intensity pulse determining the UCA destruction frame can be a single pulse or preferably a plurality of single pulses (series of pulses) applied in different directions within the imaging plane of the ultrasound imaging apparatus. The UCA destruction frame can be a single frame or a plurality of frames applied sequentially in said imaging plane. For instance, a plurality of destruction frames may be required for achieving the destruction of significant portions of microvesicles at a deeper region. As mentioned before, the applied acoustic energy level should be higher than a predetermined threshold, and capable of destroying the UCA microvesicles. In particular said level should be sufficiently high as to cause the destruction of a significant portion of the microvesicles present within the imaging plane. The destruction of a "significant portion" means that the amount of destroyed microvesicles should be sufficiently high as to allow the detection of a substantial variation of the echo signal received from the microvesicles, between the value measured right after the destruction and the time a steady perfusion state is reached. In the practice, a destruction of at least 50% of the microvesicles in the image plane is generally sufficient to obtain acceptable experimental data. Preferably, said amount of destroyed microvesicles is at least 75%, more preferably at least 90%, and up to 100% in the most preferred case.

With reference to FIG. 1a, the rate of reappearance of the UCA microvesicles in the echographic image, replenishing the region where they were destroyed, is governed, on the one hand, by the local rate of blood perfusion at each location in the image, and, on the other hand, by the acoustic sensitivity pattern of the ultrasound probe in essentially the elevation direction. The rate of this reperfusion, and more generally the values of perfusion parameters, are the unknown variables, the estimate of which may provide valuable information to a clinician for assessing local tissue pathologies.

The acoustic sensitivity pattern in elevation is the parameter that will be discussed hereafter, because its knowledge is the basis for understanding the present invention. The acoustic pressure distribution in the elevation direction y, in the field of a focusing aperture with rectangular geometry, excited in a continuous-wave mode, is approximately determined by the function:

$$p(y) \cong \Gamma \cdot \mathrm{sinc}(K_{Tx} y),$$

where $\Gamma$ is an arbitrary proportionality constant, $$K_{Tx} = \frac{2a}{\lambda \cdot z}, \quad \lambda = \frac{c}{f},$$

and the "sinc" function stands for:

$$\mathrm{sinc}(x) \equiv \frac{\sin(\pi x)}{\pi x},$$

with $f$ the ultrasound frequency, c the speed of sound in the propagating medium, $\lambda$ the ultrasound wavelength, a the transducer half-aperture in the elevation direction, z the distance from the transducer probe to the depth of interest, and y the distance off-axis in the elevation direction. [e.g. Kinsler L E, Frey A R et al., Fundamentals of Acoustics, J. Wiley & Sons, 1982]. In the case of pulsed excitation, as is generally the case in echographic imaging modes, the main lobe of the peak-pressure distribution is in close agreement with the continuous wave case, at a frequency near the center (or mean) frequency of the acoustic pulsed waveform.

As it is of interest to make a correspondence between a locally detected signal amplitude and a local UCA concentration, it is preferable to express the sensitivity patterns in terms of echo signal intensity. These patterns can be determined by the combined effects of the transmit and receive distributions, which may in general be different. In transmit, the acoustic power distribution $P_{Tx}(y)$ in the field of an ultrasound transducer, in the elevation direction, is approximately determined by the square of the pressure distribution given above. For a rectangular aperture, it can thus be expressed by a function of the form:

$$P_{Tx}(y) \cong \mathrm{sinc}^2(K_{Tx} y),$$

where $K_{Tx}$ is determined by the ultrasound transmit conditions. In practice, this power distribution can be approximated by a Gaussian function $G_{Tx}(y)$ according to:

$$P_{Tx}(y) \cong G_{Tx}(y) = e^{-(1.94 \cdot K_{Tx} y)^2}.$$

In the receive mode, a similar approximation of $P_{Rx}(y)$, where $K_{Rx}$ is determined by the ultrasound receive conditions, is:

$$P_{Rx}(y) \cong G_{Rx}(y) = e^{-(1.94 \cdot K_{Rx} y)^2}.$$

In the pulse-echo case, the power sensitivity PE(y) of the ultrasound transducer to off-axis targets is, in a first approximation, determined by the product of the transmit-beam distribution $P_{Tx}(y)$ and the receive beam distribution $P_{Rx}(y)$. The transmit-receive sensitivity-pattern PE(y) can thus be approximated by a Gaussian G(y) as:

$$PE(y) \cong G(y) = G_{Tx}(y) \cdot G_{Rx}(y) = e^{-(1.94 \cdot y)^2 (K_{Tx}^2 + K_{Rx}^2)},$$

thus leading to the definition of transmit-receive K values as determined by $$K^2 = K_{Tx}^2 + K_{Rx}^2.$$

Figure 1B:
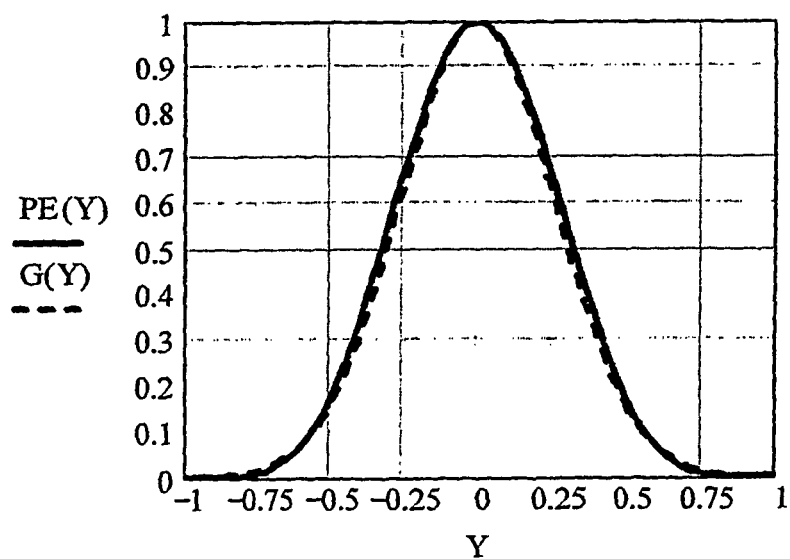
FIG. 1b is a graph showing a typical beam sensitivity distribution of an ultrasound imaging instrument, in the elevation direction.

The close correspondence of PE(Y) with G(Y) is illustrated in FIG. 1b, for the main lobe of a transducer with arbitrary rectangular geometry, for values of the unitless quantity Y≡Ky ranging from −1 to +1.

In any case, a discussion of the exact shape of this distribution is not required for describing the flow estimation methods that are the main object of this invention. Any person skilled in the art of ultrasound imaging and acoustics is able to adapt the invention to the actual beam sensitivity patterns and extent of microvesicle destruction of any given ultrasound imaging system, by determining the values of K and D at different depths or parts of the image. Such determination may be carried out by a simple calibration procedure, once and for all, for each probe and operating conditions, as explained further down.

Practically, the values of K may be determined theoretically as discussed above, or experimentally, by measuring the transmit-receive beam sensitivity by scanning a small point reflector across the image plane, in the elevation direction, and adjusting the recorded profile with a best-fit Gaussian function of the spatial displacement in elevation.

As the UCA microvesicles re-enter the slice volume, assuming first a movement in a direction perpendicular to the imaging plane, the linearized echo signal, proportional to the local concentration of UCA microvesicles, is determined by the growing proportion of microvesicles intercepted by the transmit/receive beam pattern in elevation, weighted by that beam sensitivity. For a uniform concentration of UCA microvesicles, of unity value, having re-entered the slice until position y'≡Y'/K, the echographic power signal E(Y'), resulting from the detection with the beam sensitivity PE(Y) can then be expressed, in mathematical terms, as the integral:

$$E(Y') = \int_{-\infty}^{Y'} PE(Y) \, dY \cong \int_{-\infty}^{Y'} G(Y) \, dY.$$

Implementation of the Invention using an "Error Function"

When considering the actual nature of the PE(Y) function, very close to a Gaussian function G(Y), the applicant has found it advantageous to represent the echo power signal E(Y') by using the "error function" erf(q), defined as follows [see for example: Gautschi, W., "Error Function and Fresnel Integrals," in Abramowitz, M. and Stegun, I. A. (eds.) Handbook of Mathematical Functions Dover Publications, Inc., New-York, 1972, pp. 297-329]:

$$\mathrm{erf}(q) = \frac{2}{\sqrt{\pi}} \int_o^q e^{-p^2} \, dp.$$

This definition is consistent with the properties that $$\mathrm{erf}(0) = 0,$$
$$\mathrm{erf}(-q) = -\mathrm{erf}(q) \text{ and}$$
$$\lim_{q \to \infty} \mathrm{erf}(q) = 1.$$

The physical situation of microvesicles replenishing the destroyed slice from one side (for example the negative values of Y) justifies the use of the so-called "cumulative normal distribution function", appropriately called perf(q) in this context of perfusion estimates, and defined as:

$$perf(q) \equiv \frac{1}{\sqrt{\pi}} \int_{-\infty}^{q} e^{-p^2} dp,$$

which verifies the following properties:

$$\lim_{q \to -\infty} perf(q) = 0,$$
$$perf(0) = 0.5, \text{ and}$$
$$\lim_{q \to \infty} perf(q) = 1.$$

Furthermore, perf(q) can be simply expressed in terms of erf(q) as:

$$perf(q) = 0.5 \cdot (1 + erf(q)).$$

With the above definitions, the perf function is, graphically, an S-shape function representing the energy under the Gaussian transmit-receive beam G(Y) sensitivity profile, integrated from $-\infty$ to Y, as illustrated in the example of FIG. 2, with an initial substantially flat portion (plateau) corresponding to the beginning of the reperfusion process after microvesicles destruction, a central slope portion and a final plateau corresponding to the steady state of complete perfusion. For any S-shape function according to the invention, in case the duration of the recorded data is insufficient to estimate the final steady state value, the steady state value measured just before applying the destruction pulses may be used in the fitting model as the expected asymptotic steady-state value of the reperfusion signal.

Considering a region of destroyed microvesicles of thickness D, extending symmetrically on either side of the image plane, it can be appreciated that a location is determined at a distance D/2 from the probe axis, in both the negative and positive Y directions. A flow of fresh microvesicles then replenishes the destroyed slice in the Y direction, at a flow velocity v. The echo power recovery function during the non-destructive monitoring phase, as a function of time, E(t), is thus also represented by a perf function, now expressed, in the general form, as:

$$E(t) = perf[1.94 \cdot Kv(t-D/2v)] = perf[1.94 \cdot Kv(t-\tau)],$$

where D/2v represents the time delay $\tau$ required for the microvesicles to travel from the edge of the destroyed region to the central portion of the image plane. In this way, the flow velocity v can be directly estimated experimentally from the measurement of the time delay needed for the local microvesicle concentration to reach half its maximum (or steady-state) value. This delay, which may be equated to a "mean transit time", can be readily estimated from a best-fit analysis of experimental linearized echo power signals with a parametric equation including a delay parameter $\tau$, in addition to amplitude and offset terms. For the case of a constant and uniform flow, perpendicular to the imaging plane, such parametric fit equation, F(t), can be of the form:

$$F(t) = O + A \cdot perf\left[1.94 \frac{KD}{2}\left(\frac{t}{\tau} - 1\right)\right],$$

where the parameters O, A and $\tau$ stand for offset, amplitude, and transit-time delay best-fit values, respectively, thus allowing an estimate of flow velocity in the analyzed region, using the relation v=D/2$\tau$.

The only a priori knowledge required to make this flow velocity estimate is the local thickness D of destroyed microvesicles around the scan plane, which is a value that can be mapped as a function of depth in a reasonable approximation, once and for all, for each probe type, echographic instrument, and operating mode. The value of D at different depths can be determined experimentally, for example, by embedding UCA microvesicles in a gel and estimating the extent of destroyed microvesicles by direct optical observation. Alternatively, it may be determined acoustically, in vivo or in vitro, by using a second ultrasound imaging system, at low acoustic power, with its imaging plane perpendicular to the imaging plane of the first system, to visualize the extent of destroyed UCA microvesicles. As yet another alternative, D may be estimated theoretically, on the basis of the transmit beam profile and a knowledge of the threshold in acoustic-pressure for UCA microvesicle destruction. A correction factor on the values of D with depth may be applied by taking into account tissue attenuation.

Note that, in actual practice, the UCA microvesicles replenish the destroyed zone from both sides equally; the echo power replenishment function E(t) above remains valid, since it is only the global concentration of microvesicles within the beam at each instant that matters, irrespectively of the flow direction.

Note also that, in specific circumstances, although an S-shape function according to the invention has to be associated with the echo signals in order to estimate the flow parameters, the data-set or the best-fit function may however not exhibit the S-shape characteristics of the mathematical function used for the curve-fitting in the limited time interval of the data set being analyzed. This may occur for example when only a fraction of the microbubbles is destroyed within the volume interrogated by the ultrasound beam in the elevation direction, or when, because of a limited frame rate in the presence of large flow velocities, the actual microbubble replenishment is undersampled.

In case that the angle $\theta$ between the microvesicle velocity vector and the normal to the scan plane is no longer zero, but arbitrary and different from 90°, the relation between the estimated v and the best-fit parameter $\tau$ is then simply:

$$v = \frac{D}{2\tau\cos\theta}.$$

In the absence of knowledge of the direction of flow $\theta$, the flow velocity estimated assuming $\theta=0$ then corresponds to the velocity component, $v_y$, perpendicular to the image plane.

One surprisingly remarkable feature of the present method is that estimates of a mean flow velocity along the perpendicular to the scan plane, $\bar{v}_y$, may be made even in the presence of superimposed flow contributions with different velocities $v_i$ and arising from different, arbitrary, directions $\theta_i$. This is explained hereafter. When contributed from microvesicles flowing from N different directions and/or at N different velocities, the echo signal power can be expressed as:

$$E(t) = \sum_{i}^{N} C_i \cdot perf\left[1.94 \cdot Kv_{i_y}(t - \tau_i)\right], \text{ where}$$

$$\tau_i = \frac{D}{2v_{i_y}} \text{ and}$$

$$v_{i_y} = v_i \cos\theta_i,$$

and $C_i$ is the relative concentration of microvesicles with velocities $v_{i_y}$, defined as the individual relative velocities along the y direction. In such a case, the incidence on the shape of E(t) is that it is no longer a pure perf function.

Implementation of the Invention using a "logperf" Reperfusion Function

In order to perform a successful curve fitting on such experimental reperfusion power data, i.e. arising from the sum of different flows as indicated above, it was found that it is beneficial to use an empirical parametric S-shape function of the form of a cumulative lognormal probability distribution function. This function, used in the present context, is called hereafter the logperf reperfusion function:

$$logperf(t) = O + \frac{A}{2} \cdot \left(1 + \text{erf}\left(\frac{\ln(t/\tau)}{\eta\sqrt{2}}\right)\right),$$

with $O$, $A$, $\tau$ and $\eta$ as fitting parameters. Surprisingly, the use of this logperf(t) function to fit the experimental reperfusion echo-power signal allows good estimates of a mean transit time, $\tau$mean, given by the best-fit value $\tau$. The use of the logperf parametric function as a fitting function is illustrated in FIGS. 3a and 3b. For obtaining the experimental data, a setup similar to the one described by Veltman et al. was used ("On the design of a capillary flow phantom for the evaluation of ultrasound contrast agents at very low flow velocities", Ultrasound in Med. Biol., 28(5), 625-634, 2002). A bundle of microfibres (170 fibers with 240 µm inner diameter, Hospal AN69, France) was perfused by a microbubble suspension (phospholipid-stabilized microbubbles containing perfluorobutane gas, with a mean diameter of about 2-3 µm) under control of a peristaltic pump (Gilson Minipulse 3, Villiers le Bel, France) at flow velocity values ranging from 1 to 30 mm/s. The dilution of microbubbles in distilled water corresponded to an approximate count of $10^6$ bubbles per mL flowing through the microfibers.

The echographic instrument used was an Esatune scanner (Esaote, Florence, Italy), used in CnTI(S) (Contrast Tuned Imaging) mode, with an LA532E probe used at 2.6 MHz transmit frequency and 43 Hz frame rate, at a Mechanical Index of 0.07 for the reperfusion monitoring, and using a one second sequence of destruction frames at maximum transmit power. The probe was positioned in a way to produce a cross-section image of the microfiber bundle, making an angle $\theta$ of 50° between the flow direction and the normal to the image plane. The realtime rf-signals were collected using a fast rf-grabber (FEMMINA, Scabia et al. "Hardware and software platform for processing and visualization of echographic radio-frequency signals"; IEEE Trans. Ultra. Ferr. Freq. Contr., 49(10), 1444-1452, 2002) for periods of 15 seconds for each destruction-replenishment sequence. The mean echo-power signals within a user-defined AOI were then computed to obtain the replenishment of UCA microbubbles in the microfibers, following destruction, and shown as dotted data points in FIGS. 3a and 3b, for flow velocity values of 4 and 8 mm/s, respectively.

Before fitting, the value of D was determined to be 7.2 mm by optically measuring the width of the destroyed zone in a 1.5% agarose gel containing about 5⊙$10^6$ microbubbles per mL. The logperf function was implemented in the MATLAB® Curve Fitting Toolbox (MathWorks, Natick, Mass., USA, Curve Fitting Toolbox provides graphical user interfaces (GUIs) and command-line functions for fitting curves and surfaces to data; facilitates exploratory data analysis, preprocess and post-process data, compare candidate models, and remove outliers; facilitates regression analysis using the library of linear and nonlinear models provided or custom equations; supports nonparametric modeling techniques, such as interpolation and smoothing), and the best fits were computed using the Trust Region method (Byrd, R. H., R. B. Schnabel, and G. A. Shultz, "Approximate Solution of the Trust Region Problem by Minimization over Two-Dimensional Subspaces", Mathematical Programming, Vol. 40, pp 247-263, 1988). The best fits are illustrated as solid lines in FIG. 3. The $\tau$mean values found are 1.421 and 0.6714, the $\eta$ values are 0.6197 and 0.8079, with A=1114 and 1258, for FIGS. 3a and 3b, respectively. With these $\tau$mean, $\theta$ and D values, the estimated mean flow velocity values are then 3.9 and 8.3 mm/s for FIGS. 3a and 3b, respectively, which is in good agreement with the actual values of 4 and 8 mm/s.

Figure 4A:
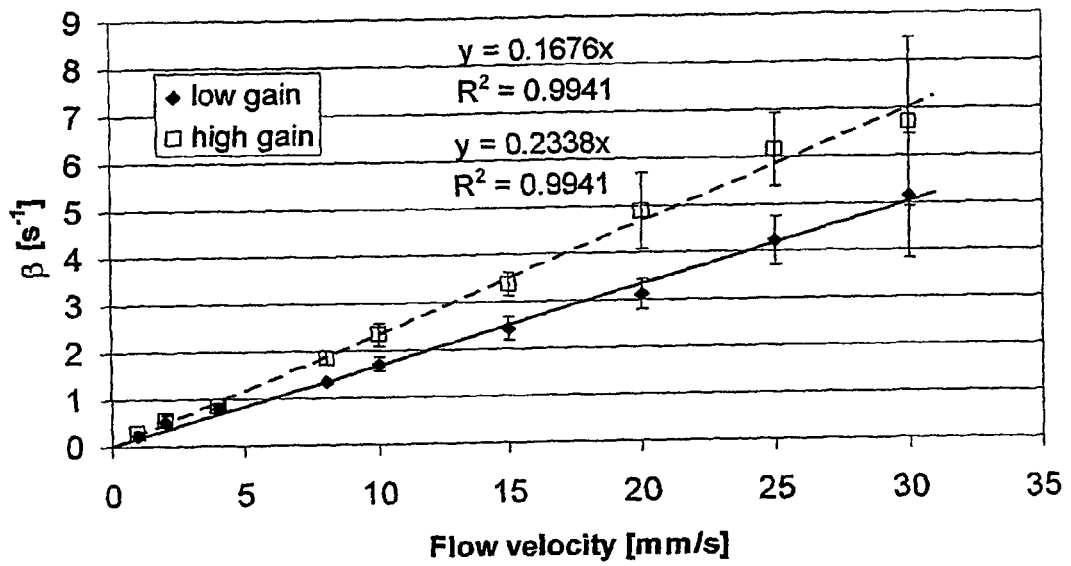
FIGS. 4a and 4b are graphs showing respectively flow velocity estimates using the prior art monoexponential fit and corresponding estimates using the method according to the invention.
Figure 4B:
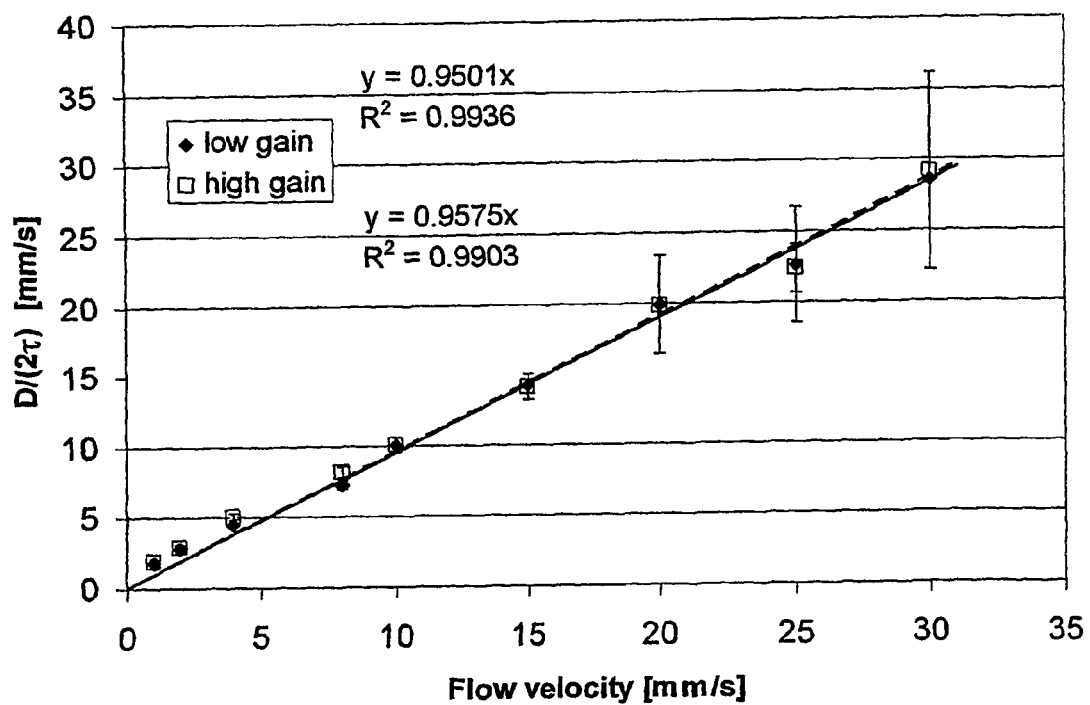

In FIGS. 4a and 4b, the main advantage of the present invention over the estimates based on monoexponential fits is illustrated, using the in vitro setup described above at increasing flow velocity values, with an angle $\theta$ of 60°, and at two different instrument gain values (high gain=2 times low gain). FIG. 4a shows the $\beta$ values obtained with the prior art monoexponential best-fits. Note the good linearity of the estimates, but with a marked difference between the two gain values used. For example, at a flow velocity of 20 mm/s, the estimated $\beta$ value is about 3.3 $s^{-1}$ at low gain, but about 4.7 $s^{-1}$ at high gain. This shows that the prior art method is system dependent. FIG. 4b shows the estimated D/(2$\tau$) values in the case of the best-fit values using the logperf function. Note the good linearity of the estimates, with absolute values of the estimates within 5% of the true values (y≅0.95× for the regression lines), for both gain values tested. In the same example of a flow velocity of 20 mm/s, the estimated D/(2$\tau$) values are about 19 mm/s, both at low and high gain values. This shows that the estimated flow velocities using the logperf function according to the invention are system independent, as well as absolute physical quantities. The parameters extracted by the method according to the invention are thus independent of the equipment or settings used, and as a result can be compared between investigators using different equipment or settings. Moreover, these extracted parameters are suitable for absolute quantitative evaluation.

Implementation of the Invention for "lognormal" Flow Distribution

The replenishment analysis of a UCA can also be used to assess best estimates of the mean, variance and skewness of a lognormal flow distribution within an unknown tissue. This may provide information relating to the organization of the microvascular network. Tissue perfusion is commonly represented as a quasi-continuum with a lognormal distribution of vessels with mean transit-time $\tau$ [Qian H. and Bassingthwaighte A. A Class of Flow Bifurcation Models with Lognormal Distribution and Fractal Dispersion. J. of Theoretical Biology, 2000, 205, 261-268]. When the tissue is perfused by microvesicles flowing at the same velocity as blood, it has been observed that the distribution of microvesicle concentrations C($\tau$) can also be described by a lognormal probability density distribution of the form:

$$C(\tau) = \frac{e^{-\frac{[\ln(\tau)-m]^2}{2s^2}}}{\tau s \sqrt{2\pi}},$$

where m and s are the mean and standard deviation of the natural logarithms of $\tau$, respectively. The mean $\mu$, variance $\sigma^2$, and skewness $\gamma$ of the lognormal distribution are given by:

$$\mu = e^{m+\frac{s^2}{2}}, \sigma^2 = e^{s^2+2m}(e^{s^2} - 1) \text{ and } \gamma = \sqrt{e^{s^2} - 1}\,(2 + e^{s^2})$$

The above probability density of transit times verifies that it is normalized to unity:

$$\int_0^\infty C(\tau)d\tau = 1.$$

As observed by the applicant, the estimation of the mean, variance and skewness of a lognormal flow distribution within an unknown tissue may be achieved by expressing the echo power E(t) as a combination of individual perf functions, weighted by the lognormal distribution of flow transit times τ. This function, called here lognormperf(t), is given by:

$$lognormperf(t) = O + A \int_0^\infty C(\tau) perf\left(1.94 \cdot \frac{K \cdot D}{2\tau}(t-\tau)\right) d\tau,$$

with all variables as defined previously.

Figure 5A:
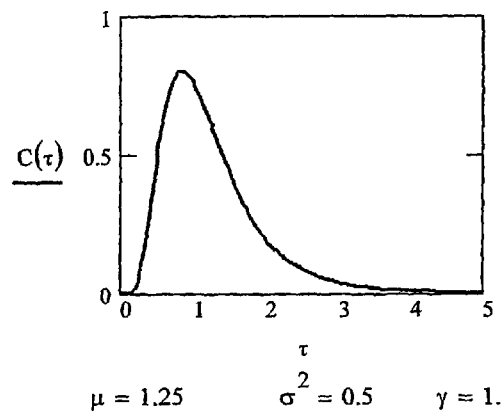
FIGS. 5a and 5b are graphs showing two lognormal probability distribution functions of flow transit time.
Figure 5B:
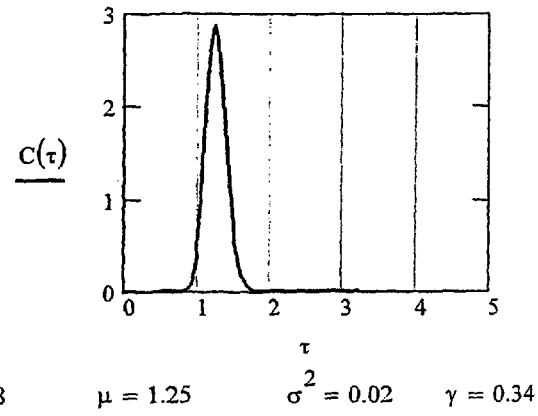

FIGS. 5a and 5b illustrate, by way of simulation examples, two lognormal distributions of transit times, one with $\sigma^2=0.5$ and $\gamma=1.88$, and the second one with $\sigma^2=0.02$ and $\gamma=0.34$, both with τmean (=μ)=1.25. These two distributions yield, with example parameters of O=0, A=1, D=7.2 mm, $\theta_i=0$ and K=1.41 $mm^{-1}$, the replenishment functions lognormperf(t)= E(t) shown in FIGS. 6a and 6b. Note that the differences between the two examples of FIG. 6 confirm that the shape of lognormperf(t)=E(t) depends on the skewness of the distributions of transit times, being very close to a perf function for a low-skewness distribution (γ=0.34) and an S-shape with a sharper rise and softer "shoulder" (inflection towards approaching the steady-state value) for the higher-skewness distribution (γ=1.88).

These latter considerations for the case of lognormal statistical distributions of transit times are illustrated, in FIGS. 7a and 7b, by way of an example using the same experimental data as in FIG. 3a. Here, the data points are fitted with the parametric expression lognormperf(t), including a lognormal distribution of flow transit times with m and s parameters. The value of K was computed to be 0.2761 $mm^{-1}$, by considering the physical conditions of the measurement, i.e. a=2.5 mm, f=2.6 MHz, z=45 mm, c=1480 mm/s, identical in transmit and receive. The values found for the best fit (with D=7.2 mm and an offset O=0) are μ=1.53 and 0.78, σ=0.47 and 0.39, γ=0.96 and 1.6, A=1114 and 1258 for the flow velocities of 4 and 8 mm/s, respectively. The two corresponding lognormal probability density distributions in flow transit time are shown on FIG. 8, and the corresponding estimated flow velocities, with θ=50°, are 3.7 and 7.2 mm/s, again in reasonable agreement with the actual imposed flow velocities of 4 and 8 mm/s, respectively.

Figure 6A:
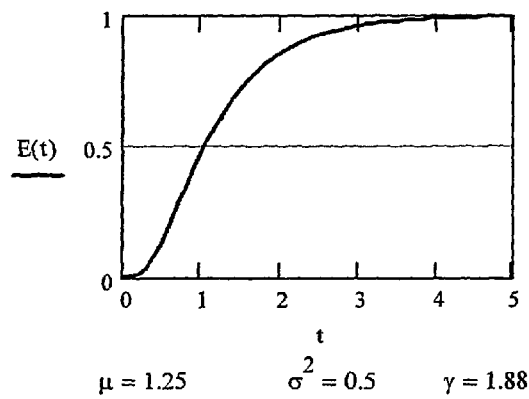
FIGS. 6a and 6b are graphs showing the S-shape echo-power reperfusion functions resulting from the flow distributions of FIGS. 5a and 5b, useful in another embodiment of the invention.
Figure 6B:
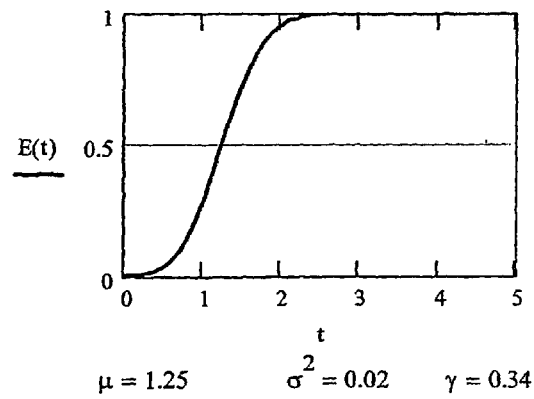
Figure 9A:
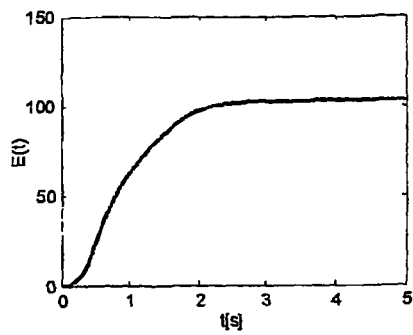
FIGS. 9a-d are graphs showing the process of wavelet decomposition of a reperfusion function, in terms of the distribution if its individual flow contributions, in a further embodiment of the invention.
Figure 9B:
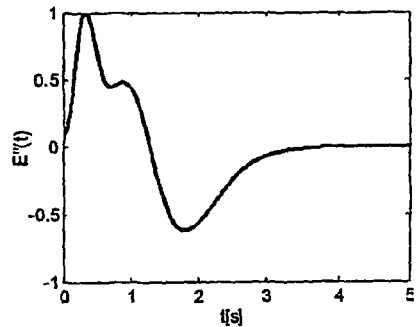
Figure 9C:
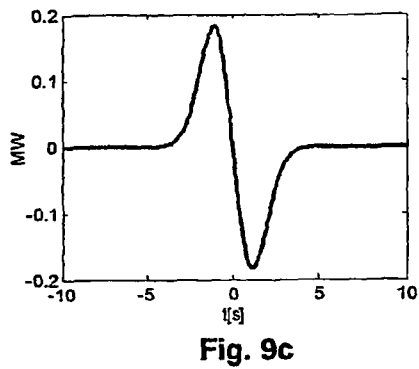
Figure 9D:
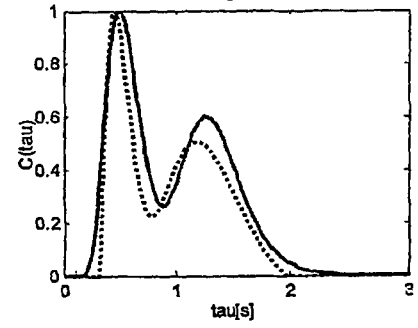

The remarkable feature in the replenishment functions of FIGS. 6a and 6b is that the corresponding estimated mean transit time values μ=τmean are in agreement, in quantitative terms, with the actual mean flow velocities, despite the fact that the two flow velocity conditions result in distributions with very different skewness values.

Thus, the parametric flow-estimates according to this invention following bubble destruction allow direct estimates of mean flow velocity in the direction perpendicular to the imaging plane, based only on the knowledge of the thickness D of destroyed bubbles at each depth of interest.

In the case of lognormal distributions of flow velocities or transit times, such as those described for representing microvasculature in various organs, the analysis of the actual shape of the reperfusion function E(t) allows an estimate of the variance and skewness of the flow distribution, and hence the possible assessment of tissue pathologies. These estimates may be made by curve-fitting power signals derived from experimental linearized echo-data, using a perf function or a linear combination of perf functions, as described above.

Implementation of the Invention with Different S-Shape Functions

While the perf function as described above correctly represents echo-energy reperfusion of single flow channels within an imaging plane with Gaussian beam-sensitivity in elevation, different equivalent parametric forms of S-shape functions, such as trigonometric functions or functions with polynomial terms, may be used as approximations of the erf function with practically acceptable accuracy. Those equivalent forms may be derived from known approximations to the erf function. Possible examples include, but are not limited to:

$$erf(q) \cong sign(q)\left\{1 - \frac{1}{1 + a_1|q| + a_2q^2 + a_3|q|^3 + a_4q^4}\right\},$$

with $a_1=0.278393$, $a_2=0.230389$, $a_3=0.000972$, $a_4=0.078108$, and sign(q)=1 for q≧0 and −1 for q<0, or:

$$erf(q) \cong \tan h(1.203 \cdot q).$$

Note that the above also implies that:

$$perf(q) \cong 0.5[1 + erf(q)] = \frac{1}{1 + e^{-2.406 \cdot q}} \equiv sigmoid(2.406 \cdot q).$$

With these approximate expressions, observed reperfusion power functions may then be fitted with perf function integrals, weighted by probability distributions of flow transit-times or velocities, such as log-normal distributions, to represent tissue perfusion. Parameters such as mean flow velocity, variance or skewness of flow-distributions may then be estimated from best fits to the observed data. These parameters may be computed within user-delimited areas of echo-energy within echographic images ("regions-of-interest"), either manually delimited by the user, automatically determined by known methods of border delineation in echographic images, or according to other anatomical organ features. Alternatively, the parameters may be computed within individual image elements such as digital video pixels (picture elements), groups of pixels, individual speckle "grains" as determined by the local imaging resolution, groups of pixel grains, or other automatically determined areas of the image, in order to be displayed as spatial parameter cartography, also called parametric imaging, without the need for the user to define the regions of interest.

Estimation of Probability Density Distribution of Transit Times or Velocities

The S-shape function obtained according to the methods described above can also be used to estimate a probability density distribution of transit times or velocities of the microvesicles during the reperfusion (for example, in the different capillaries). As it is known, in healthy tissues (i.e., without abnormalities) the microvesicles flow at the same velocity as blood; in this case, the distribution of transit times or of velocities consists of the lognormal distribution. Therefore, the estimated distribution can be used to detect physiological anomalies, by simply comparing it with the lognormal distribution.

New methods of calculating the probability density distribution functions have been developed, which are particularly advantageous when used in the proposed method where a correspondence is made between at least one value of a parameter of said function with S-shape characteristics with the local tissue perfusion value or attribute. The below-described new methods are however also valuable for providing calculation of probability density distribution functions in other perfusion analysis contexts, for example in the case of a bolus administration of UCA, characterized e.g. by a linear increase and an exponential decay of echo power as a function of time.

Implementation of the Invention by Wavelet Analysis

The reperfusion echo data may be analyzed with the view that it is the result of an unknown sum of individual perf functions, rather than resulting from lognormal or normal distributions of transit times. In such a case, it has been found that a continuous wavelet decomposition, applied on the second time derivative of the perfusion function, or a smoothed or low-pass filtered version of the perfusion function, provides a useful estimate of the probability distribution of flow transit times. Here, the "mother wavelet" (or model wavelet) for the estimate of the wavelet scale and delay coefficients can be naturally chosen as the second derivative of a perf function with velocity $v_{mw}$. Such function satisfies all the requirements of the definition of a wavelet. The scale sc and delay del coefficients of the continuous wavelet transform, in a digital form, are taken, in this context of UCA replenishment of a bubble destruction zone, as:

$$sc = \frac{2\tau \cdot v_{mw}}{D \cdot dt} \text{ and } del = \frac{\tau}{dt},$$

where dt represents the sampling time interval.

FIG. 9 illustrates the process of estimating an arbitrary distribution of transit times, using the continuous wavelet transform on the second time derivative of a reperfusion curve. The theoretical reperfusion example of FIG. 9a is the one to analyze, actually given by a bimodal distribution of transit times with mean values centered around 0.56 and 1.35 seconds, respectively. The second derivative of this function is shown, on a relative amplitude scale, in FIG. 9b. The mother wavelet chosen to perform the wavelet decomposition is shown in FIG. 9c, actually taken as the second derivative of an elementary perf function. In FIG. 9d, the result of the wavelet decomposition is compared, in acceptably good agreement, with the original bimodal distribution of transit times used to generate the reperfusion function of FIG. 9a, confirming the practical applicability of wavelet analysis within the context of flow distribution estimates of the present invention. Similar analyses of the reperfusion function can be performed to estimate distributions of transit times, using Fourier, Radon, Hilbert, Z- or any other integral transforms, based in each case on the recognition that individual values of perfusion transit times generate individual power contributions, as a function of time, of the type of the perf function disclosed in this document.

Alternatives to fitting the observed reperfusion data with the approaches described above include the following: it may be advantageous in some cases to apply any known form of smoothing or time averaging to the experimental data, such as moving average, low-pass filtering, median filtering, etc., or any combination of the above, before performing the curve fitting. Yet another alternative could be to perform the curve fitting on the "non-linearized" echo data (e.g. log-compressed data) with the S-shaped fitting functions, disclosed in the present invention, modified by the same process as the one causing the nonlinear responses of the echo signals (e.g. log-compression of the S-shaped functions).

Reconstruction of Probability Density Distributions of Flow Velocities using Neural Network Analysis In a different embodiment of the invention, the reperfusion echo data is instead analyzed by a one step or multiple step process.

The starting point of the analysis is the above-described echo power replenishment signal E(t).

Repeating the relevant formulas for the sake of clarity, the Pulse-Echo acoustic sensitivity pattern PE(y) in the elevation direction can be approximated by a Gaussian G(y):

$$PE(y) \cong G(y) := e^{-(1.94 \cdot y)^2 \cdot K^2} \quad (1.1),$$

Advantageously, the replenishment function E(t) is represented as:

$$E(t) = perf(t), \quad (1.2)$$

$$\text{where } perf(t) := O + A \cdot \phi(1.94 \cdot Kv(t-\tau)), \quad (1.3)$$

$$\phi(q) = 0.5 \cdot (1 + \mathrm{erf}(q))$$

and $$\mathrm{erf}(q) = \frac{2}{\sqrt{\pi}} \int_0^q e^{-p^2} dp$$

and O is the offset factor, A is the amplitude factor and $$\tau = \frac{D}{2v} \quad (1.4)$$

is the transit time required for the microbubbles to travel from the edge to the center of destroyed zone.

In case the angle $\theta_v$ between the microbubble velocity vector v and the y direction is no longer zero, but arbitrary and different from 90°, the definition (1.3) of perf (t) becomes $$perf(t) := O + A \cdot \phi(1.94 \cdot K' v(t-\tau)), \quad (1.5)$$

$$\text{where } K' := K \cdot \cos\theta_v \text{ and}$$

$$\tau = \frac{D'}{2v},$$

$$\text{where } D' := \frac{D}{\cos\theta_v}.$$

Let $v_y$ be the component of v along the y direction, i.e.

$$v_y = v \cdot \cos\theta_v; \quad (1.6)$$

Then $$perf(t) = O + A \cdot \phi(1.94 \cdot K \cdot v_y(t-\tau_y)),$$

$$\text{where } \tau_y = \frac{D}{2v_y}.$$

It is noted that (1.6) is equivalent to the definition (1.3) with $v_y$ instead of v and $\tau_y$ instead of τ. Perf(t) (1.6) can be written more correctly in terms of either $v_y$ alone or $\tau_y$ alone:

$$\text{perf}_{v_y}(t) := O + A \cdot \phi\left(1.94 \cdot K \cdot v_y\left(t - \frac{D}{2v_y}\right)\right), \quad (1.7)$$

$$\text{perf}_{\tau_y}(t) := O + A \cdot \phi\left(1.94 \cdot K \frac{D}{2\tau_y}(t - \tau_y)\right). \quad (1.8)$$

In a region of interest there are many capillaries and every capillary is characterized by one and only one velocity of reperfusion. Hence the replenishment function of every capillary is given by (1.7) or (1.8) (individual perf functions):

$$E(t) = \text{perf}_{v_y}(t)$$

or, equivalently, $$E(t) = \text{perf}_{\tau_y}(t).$$

If $P(v_y)$ is the probability density distribution of component of velocities along the y direction in a region of interest, the echo power replenishment function E(t) in such a region can be expressed as a combination of individual perf functions, weighted by the probability of influence of each capillary:

$$E(t) = \int P(v_y) \cdot \text{perf}_{v_y}(t) dv_y. \quad (1.9)$$

The discrete version of (1.9) is $$E(t) = \sum_{i=1}^{n} P(v_{i_y}) \cdot (v_{i+1_y} - v_{i_y}) \cdot \text{perf}_{v_{i_y}}(t). \quad (1.10)$$

The probability density distribution P(v) satisfies the normalization property:

$$\int P(v_y) dv_y = 1, \quad (1.11)$$

so that $$\sum_{i=1}^{n} P(v_{i_y}) \cdot (v_{i+1_y} - v_{i_y}) \cong 1. \quad (1.12)$$

In terms of $\tau_y$:

$$E(t) = \int P(\tau_y) \cdot \text{perf}_{\tau_y}(t) d\tau_y,$$

whose discrete version is $$E(t) = \sum_{i=1}^{n} P(\tau_{i_y}) \cdot (\tau_{i+1_y} - \tau_{i_y}) \cdot \text{perf}_{\tau_{i_y}}(t), \quad (1.13)$$

where $P(\tau_y)$ is the probability density distribution of $\tau_y$ in the region of interest; thus, analogously to (1.11) and (1.12), $$\int P(\tau_y) d\tau_y = 1 \quad (1.14)$$

and $$\sum_{i=1}^{n} P(\tau_{i_y}) \cdot (\tau_{i+1_y} - \tau_{i_y}) \cong 1.$$

To simplify the notation, in the following the subscript Y will be omitted; thus, notation v and τ will be used instead of $v_y$ and $\tau_y$, which will be referred to as velocity and transit time, respectively.

When microbubbles flow at the same velocity as blood, characterizing healthy tissue (without abnormalities), P(v) is a lognormal probability density distribution:

$$P(v) = \frac{e^{\frac{-(\ln(v)-m)^2}{2s^2}}}{vs\sqrt{2\pi}},$$

where m and s are respectively the mean and the standard deviation of the natural logarithms of v.

Analogously, in terms of τ, healthy tissue is characterized by $$P(\tau) = \frac{e^{\frac{-(\ln(\tau)-m)^2}{2s^2}}}{\tau s\sqrt{2\pi}},$$

where m and s are respectively the mean and the standard deviation of the natural logarithms of τ.

Figure 10:
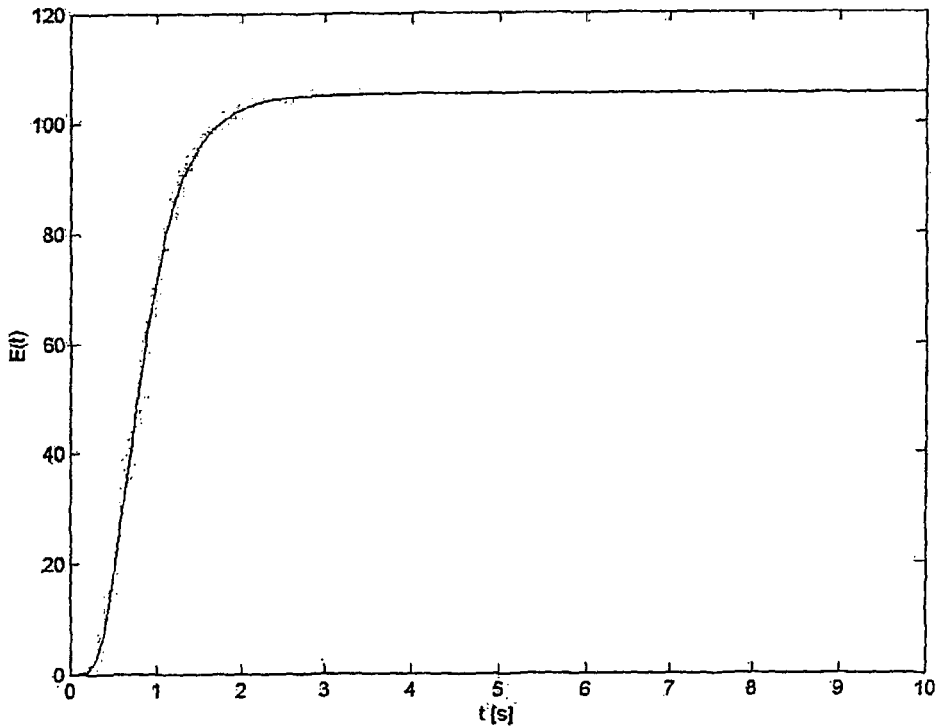
FIGS. 10 to 14 are graphs illustrating analysis of echo-power data to estimate the distribution of contributions at different flow transit times or velocities, by a one step process, or the first step of a multi-step process.

FIG. 10 illustrates an example of replenishment function in the lognormal case. To construct this curve formula (1.10) has been used, where:

parameters of lognormal probability density distribution: m=1.5, s=0.45;

vector of velocities:

$$v_1 = v_{min} \cdot b^0, \ldots, v_n = v_{min} \cdot b^{n-1}, \quad (1.15)$$

where $b = e^{\frac{\ln(v_{min}/v_{max})}{n-1}}$, $v_{min} = 1$, $v_{max} = 25$, $n = 32$.

Equations (1.10) and (1.13) express the replenishment function as a linear combination of (individual) perf functions. The actual echo power replenishment signal can be expressed as $$E'(t) = E(t) + N(t),$$

where E(t) is the (theoretical) replenishment function and N(t) represents noise.

Hence a vector of signals recorded at the instants $t_1, \ldots, t_j$ of the replenishment phase can be written as $$E' := (E'(t_1), \ldots, y(t_j)) = (E(t_1), \ldots, E(t_j)) + (N(t_1), \ldots, N(t_j)). \quad (1.16)$$

The objective is to find a good approximation of $P(v_i)$ or, equivalently, $P(\tau_i) \; \forall i$ from E', without assuming any information about the form of P(v) or P(τ).

In the following, the problem formulation will be indifferently handled in terms of σ and τ; in particular the reconstruction of either P(v) or P(τ) will be indifferently illustrated. A new single or multi-step method has been developed, which can be advantageously implemented by using the MATLAB® Optimization Toolbox for the first step and the MATLAB® Neural Network Toolbox for the second and further steps.

Implementation of the First Step

Let E' be defined by (1.16) and let sum_perf(p, t) be a function defined by the linear combination:

$$\text{sum\_perf}(p, t) = \sum_{i=1}^{n} p_i \cdot \text{perf}_{v_i}(t),$$

where $p=(p_1, \ldots, p_n)$ is a vector of weight factors, and n is the number of flow velocities considered for the analysis. Let then sum_perf (p) be the vector defined by $$\text{sum\_perf}(p) := (\text{sum\_perf}(p,t_1), \ldots, \text{sum\_perf}(p,t_j)) \quad (1.17)$$

If sum_perf is considered as a function of p, a function $f$ of p (error function) can be defined as $$f(p) = \sum_{k=1}^{j} |\text{sum\_perf}(p, t_k) - E'(t_k)|.$$

The objective is thus to find the minimum of the constrained nonlinear multivariable function $$P(v_i) \cong \frac{(P_{\min})_i}{v_{i+1} - v_i} \forall i = 1 \ldots n. \quad (1.19)$$

in fact, if it is possible to find a solution $p_{min}$ of the constrained function (1.18) an approximation of $P(v_i)$ can be found by means of this simple rule:

$$\min_{p} f(p) \text{ subject to } p_i \geq 0 \ \forall i = 1 \ldots n; \quad (1.18)$$

Moreover an approximation of the replenishment function can be as follows:

$$E(t) \cong \text{sum\_perf}(p_{min}, t). \quad (1.20)$$

The MATLAB® programming language contains a toolbox called Optimization Toolbox especially useful for solving minimization problems. In particular the MATLAB® function fmincon finds the constrained minimum of a scalar function of several variables starting at an initial estimate. The fmincon function uses a subspace trust region method based on the interior-reflective Newton method described in Coleman, T. F. and Y. Li, "An Interior, Trust Region Approach for Nonlinear Minimization Subject to Bounds", SIAM Journal on Optimization, Vol. 6, pp. 418-445, 1996 and in Coleman, T. F. and Y. Li, "On the Convergence of Reflective Newton Methods for Large-Scale Nonlinear Minimization Subject to Bounds", Mathematical Programming, Vol. 67, Number 2, pp. 189-224, 1994. Each iteration involves the approximate solution of a large linear system using the method of preconditioned conjugate gradients (PCG).

The analytic formula for the gradient of $f$ has been supplied to fmincon so that the gradient is not calculated numerically and the algorithm becomes more precise. The choice of initial estimate to assign to fmincon is rather important. In fact the (constrained) function $f$ has many local minima that allow to find a good approximation of the replenishment function E(t), but not a good approximation of $P(v_i)$.

In the case of $N(t_k)=0 \ \forall k=1, \ldots, j$, very good results were obtained by using these initial estimates:

$$(p_{initial})_i = \frac{1}{n} \ \forall \ i = 1 \ldots n \quad (1.21)$$

$$(p_{initial})_i = (v_{i+1} - v_i) \cdot (\max(v_1, \ldots, v_n) - \min(v_1, \ldots, v_n)), \quad (1.22)$$
$$i = 1 \ldots n$$

Velocities values in a given interval of interest can be selected according to an arithmetic or geometric progression thereof.

Figure 11:
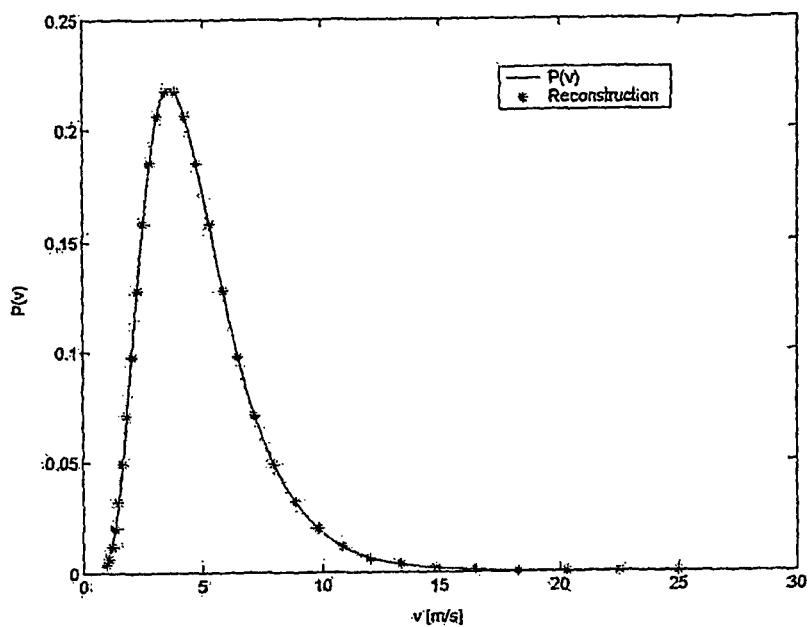

FIG. 11 illustrates the reconstruction of P(v) from a sample of the replenishment function E(t) shown in FIG. 10. The algorithm with the vector of velocities (1.15) (the same used to construct the sample of FIG. 10, i.e. with n=32) and the initialization (1.22) have been applied.

Figure 12:
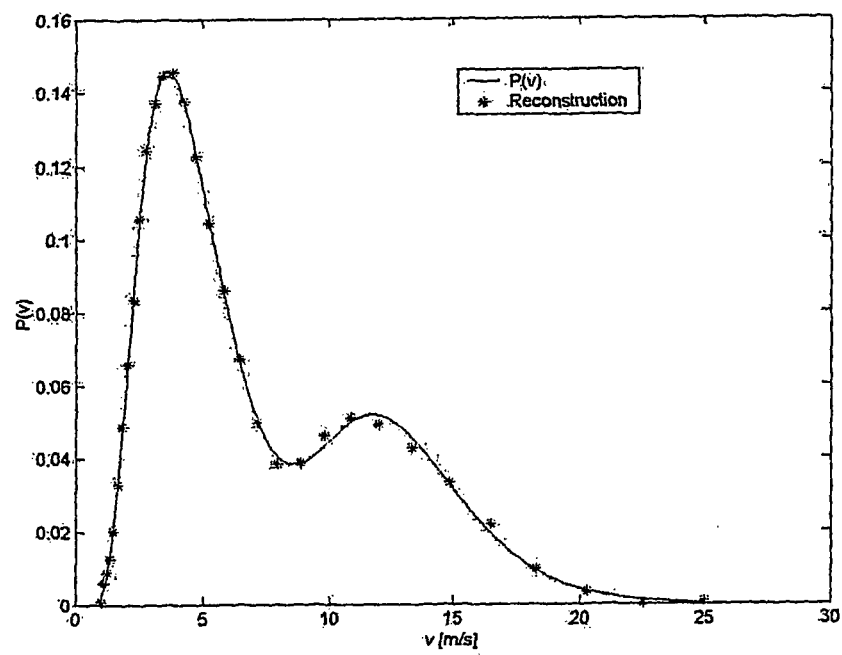

FIG. 12 illustrates the reconstruction in a case of a bimodal probability density distribution $$P(v) = \frac{2}{3} lognormal(v, m_1, s_1) + \frac{1}{3} lognormal(v, m_2, s_2),$$

where $m_1 = 1.5, s_1 = 0.45, m_2 = 1.7 \cdot m_1, s_2 = \frac{s_1}{2}.$

To understand whether the algorithm can be effective in the case of actual experimental signals, it has been applied to a sample constructed in the following way:

$$E'(t)=E(t)+N(t) \quad (1.23)$$

where N(t) is white noise temporal signal with a 10% energy amplitude compared to the instantaneous signal.

Figure 13:
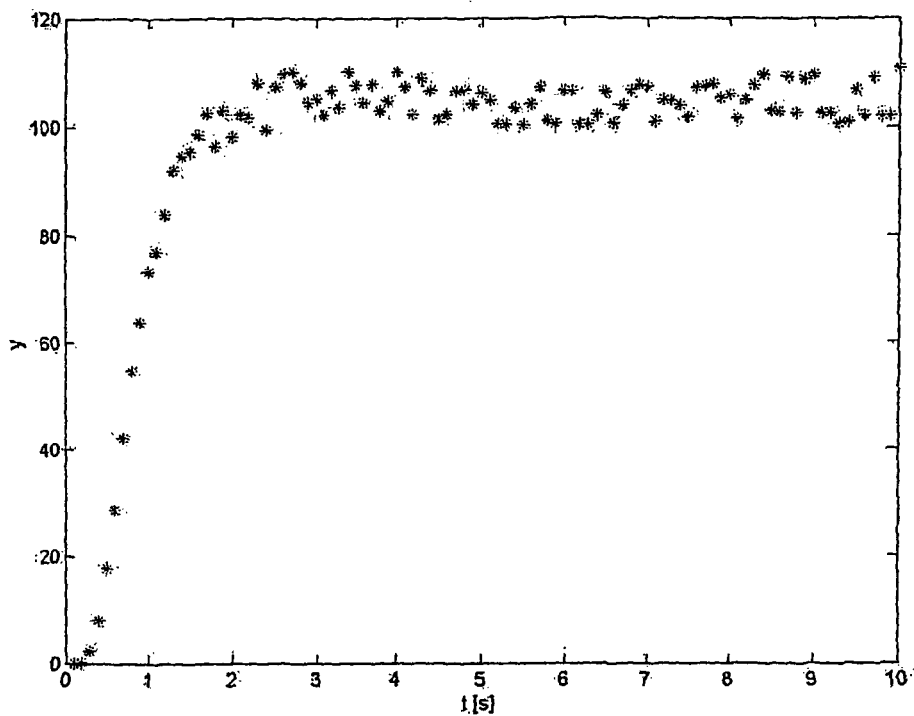
Figure 14:
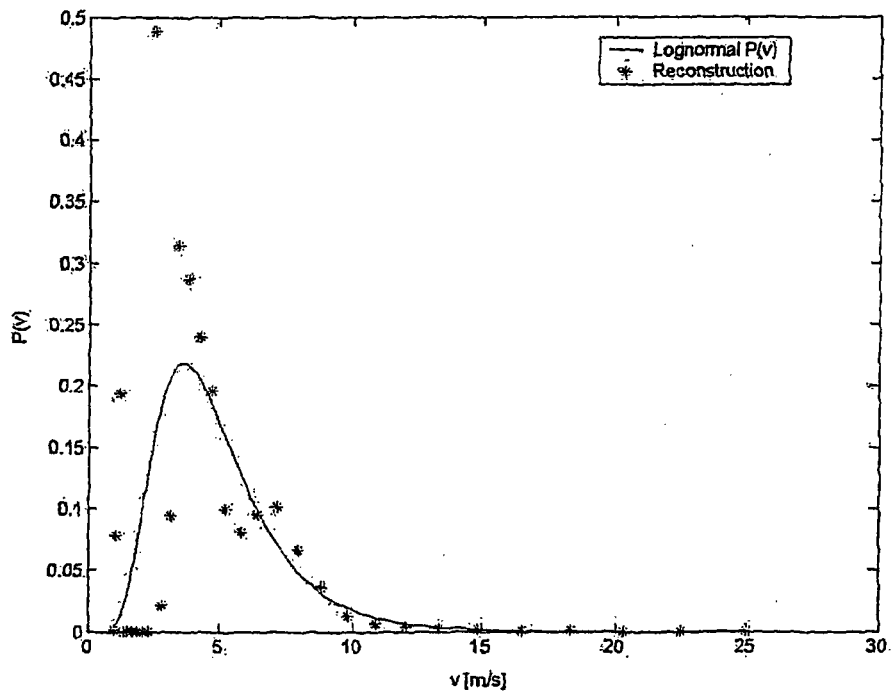

FIG. 13. shows a "noisy" sample constructed with (1.23) in a case of lognormal P(v) and FIG. 14 the reconstruction of lognormal P(v) found from this noisy sample.

FIG. 14 clearly shows that accuracy can be lost in case of relatively high noise. This "one-step" method is therefore particularly useful for samples with low noise. For samples with noise, it is advantageous to complete the method with second and third steps, as described below and reduce the number of velocities n considered in the first step.

Implementation of the Second and Third Steps:
(Neural Network)

The elementary object of a neural network is a neuron. The model of a simple neuron can be described as follows: a scalar input u is transmitted through a connection that multiplies its strength by the scalar weight p, to form the product p·u, again a scalar; then the sum of p·u and a bias b is the argument of a transfer function g, which produces the scalar output a. Typically the transfer function is a step function or a sigmoid function or the identity function (id).

Figure 15:
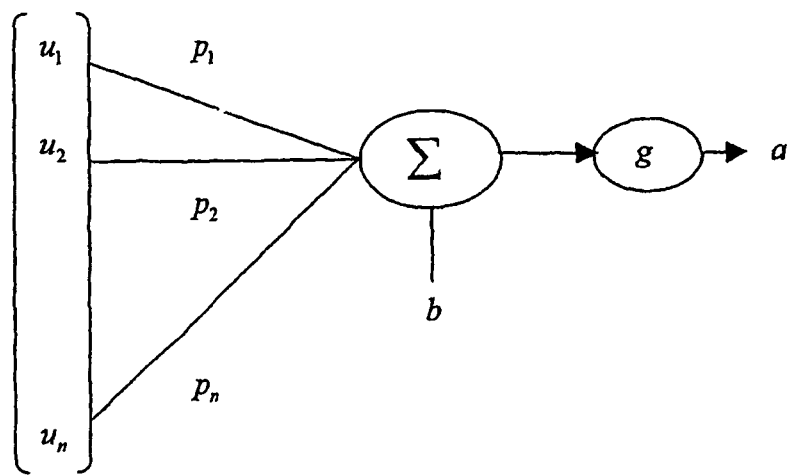
FIG. 15 is a diagram illustrating a neural network.

In a neuron with vector input, the input u is a vector u= $(u_1, \ldots, u_n)$ and p is a vector of weights; the inner product p·u is summed with the bias b to form the argument of the transfer function g, which produces the scalar output a, as illustrated in FIG. 15.

Two or more neurons as described earlier can be combined in a layer, and a neural network could contain one or more such layers. However it is not necessary to consider these more complicated networks in detail; in fact, it is sufficient to use a network formed by only one neuron with vector input.

Let net be a network of this type and let g:=id be its transfer function. Net can be created with the MATLAB® function newlin.

Neural networks can be trained, by adjusting the values of the weights and the bias, so that a particular input leads to a specific output. Hence, for training process of the network net, an input vector $u_1, \ldots, u_n$ and a corresponding target output vector $a=(a_1, \ldots, a_n)$ are needed. During training, the weights and biases of the network are iteratively adjusted to minimize the network performance function (net.performFcn). The default performance function for networks created with newlin is mean square error (mse), the average squared error between the network outputs w=g (p□u+b)=id (p□u+b)=p□u+b and the target outputs a:

$$mse = \frac{1}{n}\|w - a\|^2.$$

Let $u_i$ be the column vector defined by $$u_i(k) := perf_{v_i}(t_k) \forall i=1,\ldots,n, \forall k=1,\ldots,j; \quad (1.24)$$

let a be the vector defined by $$a := E' \quad (1.25)$$

Since $$p \Box u = \text{sum\_perf}(p, t_k) \ \forall \ k = 1, \ldots, j,$$

then $$mse = \frac{1}{j}\sum_{k=1}^{j}(\text{sum\_perf}(p, t_k) + b(t_k) - E'(t_k))^2,$$

where sum_perf (p) is defined by (1.17).

As described above, during training, the weights and bias of the network are iteratively adjusted to minimize mse; if the bias value is initialized to zero and it is kept very close to zero during all the training process, then this minimization problem is very similar to the problem (1.18) in the above-mentioned first step.

In addition to the bias value problem, other problems have to be solved: how to constrain weights to be positive or zero and how to choose the initial estimates of weights. The following approach has been adopted:

1. bias value: the bias value is initialized to 0 and every 50 or 100 iterations it is reset back to 0;
2. initial estimates of weights: the optimization algorithm described in the previous section is applied with a vector of only 8 velocities $v_{eight}=(v_{eight_1}, \ldots, v_{eight_8})$, uniformly distributed; in this way, by means of (1.19), 8 approximations of $P(v_{eight_1}), \ldots, P(v_{eight_8})$ are determined for the first step of the analysis. By fitting these 8 values in the velocity domain with a cubic smoothing spline (MATLAB® function csaps), by evaluating this spline at $v_1, \ldots, v_n$, again uniformly distributed, and finally by multiplying every value by $v_{i+1}, \ldots, v_n$, n initial estimates of weights are obtained for the second step of the analysis, where n can be any value larger than the one chosen for the first step (e.g. n=32 in the case of FIGS. 16-18); in general, it has been observed that the initial number of velocities to be considered in the first step of the analysis is from 4 to 16, preferably 6 to 10, while for the second step the number of velocities to be considered is from 8 to 64, preferably from 16 to 48;
3. non-negativity constraints on weights: every 50 or 100 iterations all negative weights are replaced by zero.

Very good results have been obtained by using these rules and the training MATLAB® function traingdx. Traingdx updates weight and bias values according to batch gradient descent momentum and an adaptive learning rate:
  gradient descent: the gradient descent algorithm updates the network weights and biases in the direction in which the performance function mse decreases most rapidly, i.e. the direction opposite to the gradient. One iteration of this algorithm can be written $$W_{I+1} = W_I - \alpha_I g_I,$$

where $W_I$ is a vector of current weights or current bias, $g_I$ is the current gradient, and $\alpha_I$ is the learning rate.
  batch mode: in batch mode the weights and the bias of the network are updated only after the entire training set has been applied to the network;
  gradient descent with momentum: momentum is a technique that can be added to the gradient descent algorithm and allows a network to respond not only to the local gradient, but also to recent trends in the error surface. Acting like a low-pass filter, momentum allows the network to ignore small features in the error surface;
  adaptive learning rate: the performance of the gradient descent algorithm can be improved if the learning rate is allowed to change during the training process.

Moreover, to reduce the negative effect of noise, a median filter (MATLAB® function medfilt1) has been applied to the noisy vector E' before applying the new algorithm.

The results are presented below.

Before illustrating the results, it seems worth illustrating the advantage of replacing all negative weights and current bias by zero only every 50 or 100 iterations and to illustrate the rationale of the stopping criterion.

During training iterations the value of the performance function mse decreases; but when the algorithm is stopped to replace all negative weights and current bias by zero, the values that the training process has found are modified, and mse consequently increases. Hence the iterations start again from a higher value of the performance function.

If the number J of iterations before stopping is too small, then mse does not decrease enough before increasing and the algorithm can be less effective.

Figure 16:
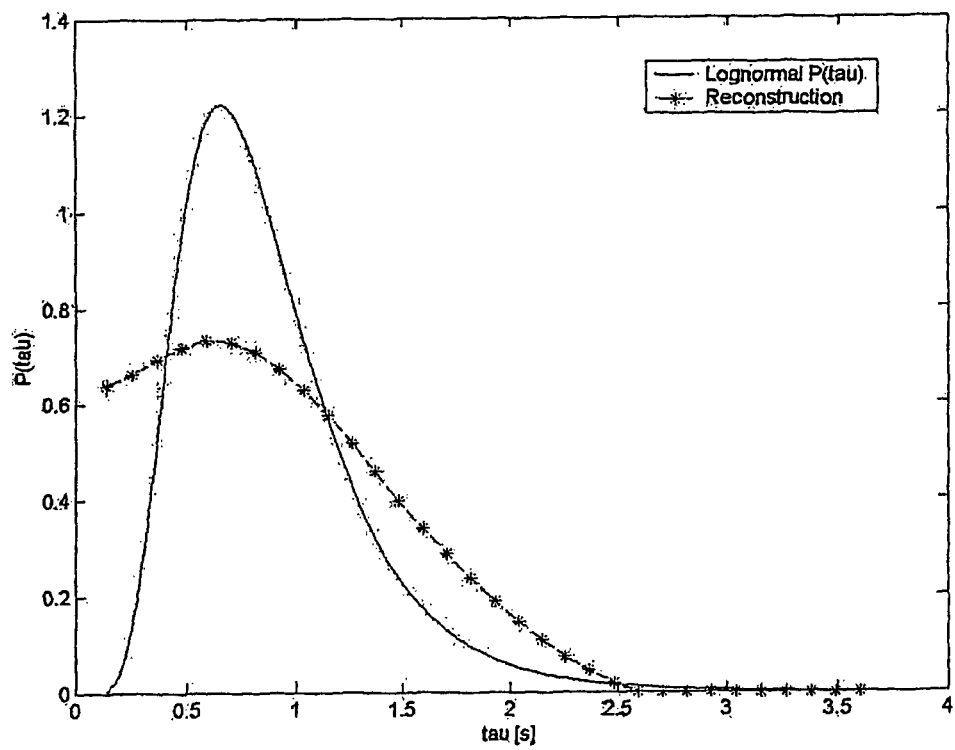
FIGS. 16 to 34 are graphs illustrating analysis of echo-power data to estimate the distribution of contributions at different flow transit times or velocities, by subsequent steps of a multi-step process.
Figure 17:
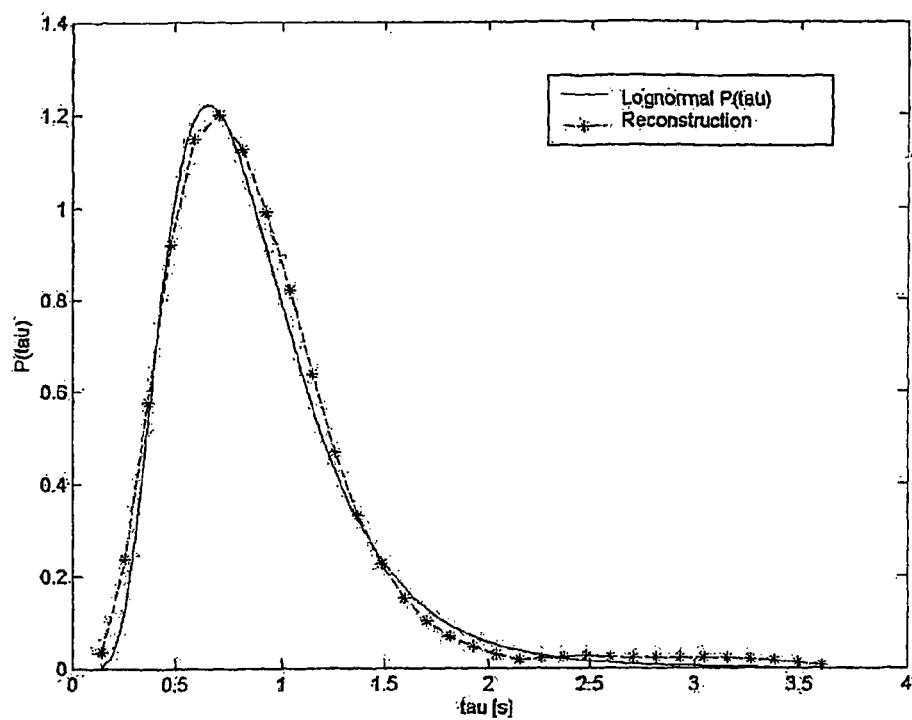
Figure 18:
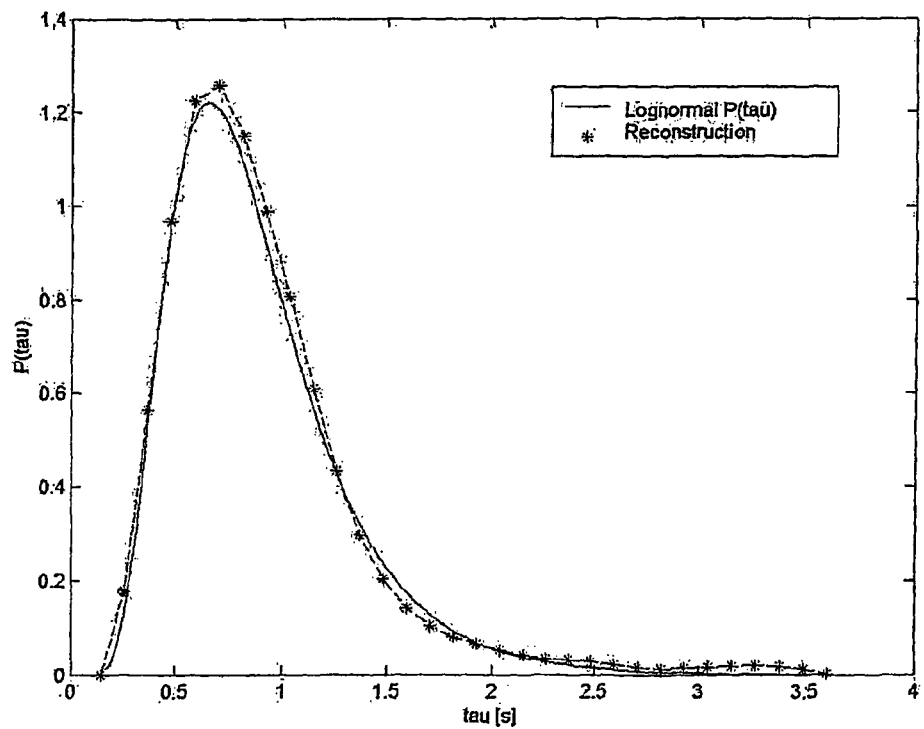

It has been empirically observed that, in the specific example illustrated in FIGS. 16-18, J should preferably be 50 or larger, to have the best results. In general, the value of J shall preferably be at least 10, more preferably at least 25 and even more preferably at least 50, up to about e.g. 200, typically about 100.

As for the applied stopping criterion, said stop intervenes when the relative change in the mse falls below a specified tolerance tol. Note that the relative change in mse is not measured after each iteration, but whenever negative weights and current bias are replaced by zero. Then the total number of iterations is always a multiple of J.

Although the first and second steps have been described in terms of ν, they could instead be described in terms of τ. The only difference is that a vector of τ is used instead of ν to construct the sample E' and to analyze it with the algorithms.

FIGS. 16, 17 and 18 illustrate the reconstruction of a log-normal P(τ) (m=−0.2191, s=0.45) from the same noisy E' (10% white noise), with n=32 and J=25,50,100, respectively. In any case the algorithm stopped because the relative change in mse fell below the tolerance tol=0.01, but there is a sensible difference between the final absolute value of mse for J=25 and the final absolute value of mse for J=50,100. Table 1 contains initial and final values of mse. It is clear that in the specific example the choice of J=25 does not allow the mse to decrease enough to have a good reconstruction of P(τ).

TABLE 1

Initial and final values of mse.

|  | Initial mse | final mse |
|---|---|---|
| J = 25 | 111.434 | 12.5768 |
| J = 50 | 111.434 | 0.5925 |
| J = 100 | 111.434 | 0.4729 |

When synthetic data E' are constructed by means of Equation (1.23), a given value for the offset factor O and a given value for the amplitude factor A are used. In this case these known values can be used when applying the algorithm. Otherwise, when dealing with real data, it can be assumed that O=0, but the value of the amplitude is unknown. A first approximation of A can be given by assuming the asymptotic value of E' and use this value for the analysis. However, this may not be a completely satisfactory way of dealing with the problem; hence, to improve the efficiency of the approach in the real case, it can be modified as follows:

let $$\bar{perf}_\tau(t)$$

be a modification of $perf_\tau(t)$ defined by $$\bar{perf}_\tau(t) = \phi\left(1.94 \cdot K \frac{D}{2\tau}(t-\tau)\right);$$

so that the replenishment function can be expressed as $$E(t) = \sum_{i=1}^{n} A \cdot P(\tau_i)(\tau_{i+1} - \tau_i)\bar{perf}_{\tau_i}(t). \quad (1.26)$$

The algorithm can thus be applied with this new $$\bar{perf}_\tau(t)$$

instead of $perf_\tau(t)$. From now on, this new version of the algorithm will be referred to as "final algorithm". The only difference with the old version is that an approximation $[A \cdot P(\tau_i)]_{est}$ of $A \cdot P(\tau_i)$, instead of $P(\tau_i)$, is found.

In the synthetic cases, in which the real amplitude is known, $[A \cdot P(\tau_i)]_{est}$ can be compared with the real $A \cdot P(\tau_i)$. Moreover, since the probability density function satisfies Equation (1.14), it follows that $$\sum_{i=1}^{n} A \cdot P(\tau_i) \cdot (\tau_{i+1} - \tau_i) \cong A.$$

Hence an approximation of A can be found as follows:

$$A_{est} := \sum_{i=1}^{n} [A \cdot P(\tau_i)]_{est} \cdot (\tau_{i+1} - \tau_i).$$

Figure 19:
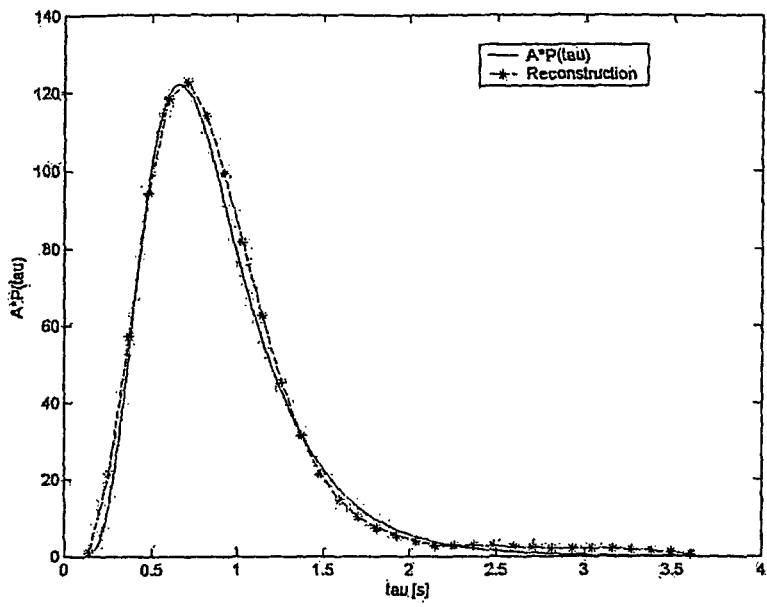
Figure 20:
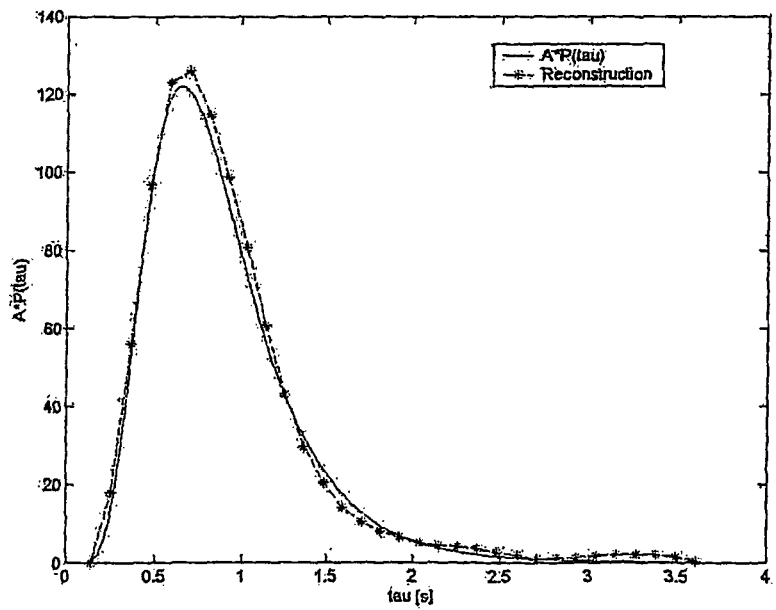

FIGS. 19, 20 illustrate the reconstruction of P(τ) from the same E' of FIGS. 16, 17, 18 by means of the final algorithm, with J=50,100 respectively; tol is 0.01. The real value of amplitude is A=100.

As explained above, the objective is to find a good approximation of P(v) or, equivalently, of P(τ), without assuming any information about its form. Reconstructions of several probability density distributions found with the above-mentioned final algorithm are illustrated in the following, always with 10% of white noise.

Figure 21:
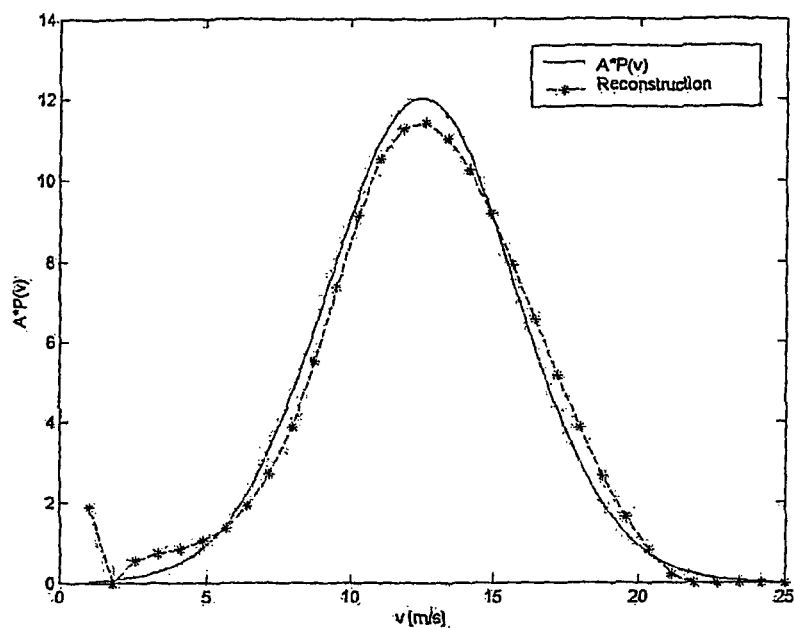

FIG. 21 illustrates the reconstruction of the Gaussian P(v) with mean μ=12.5 and variance $\sigma^2$=11, i.e. with mean A·P(v); P(v) Gaussian; J=50; tol=0.01.

Figure 22:
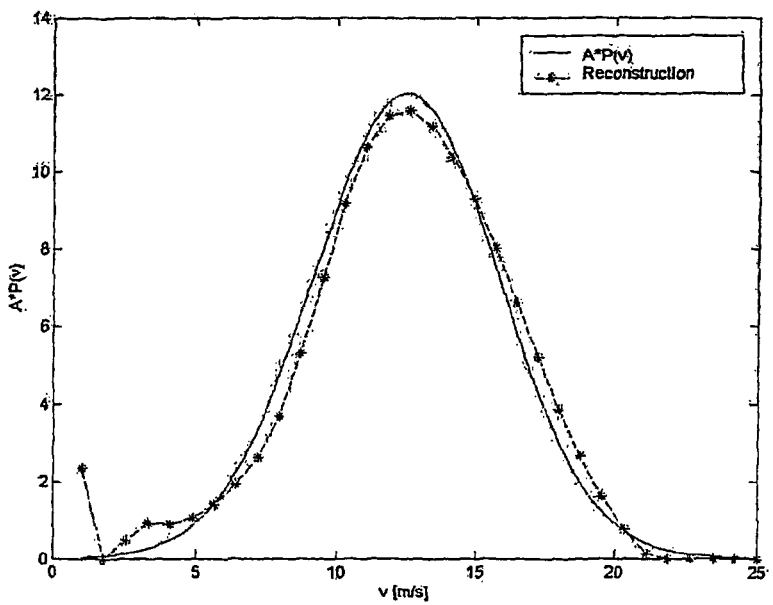

FIG. 22 represents the reconstruction of A·P(v); P(v) Gaussian; J=100; tol=0.01.

Figure 23:
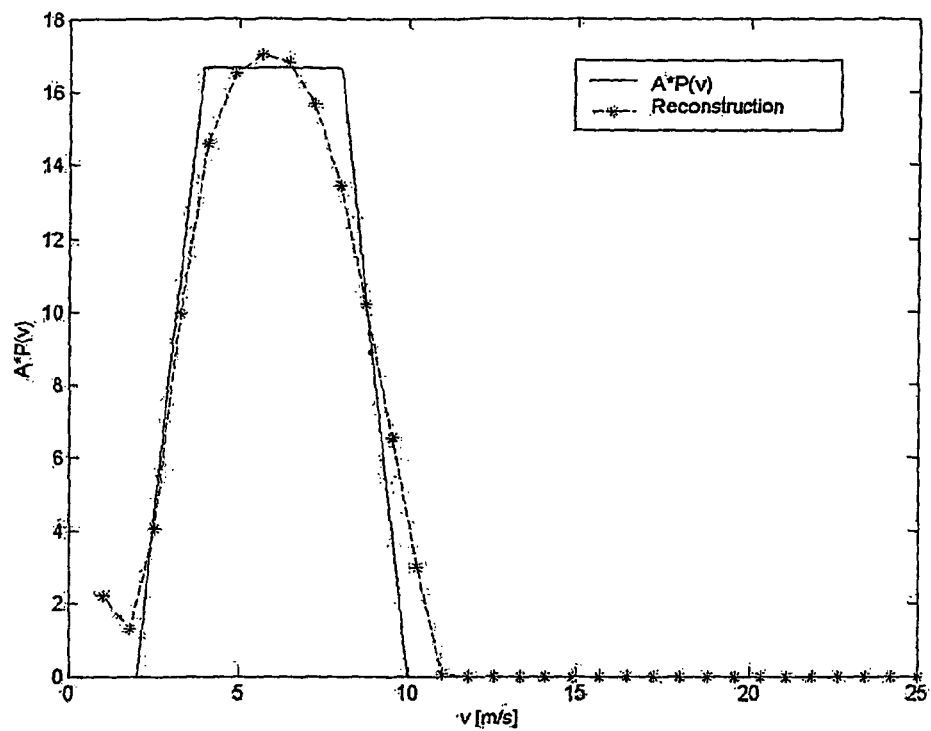

FIG. 23 represents the reconstruction of a trapezoidal P(v), namely the reconstruction of A·P(v); P(v) trapezoidal; J=50; tol=0.01.

Figure 24:
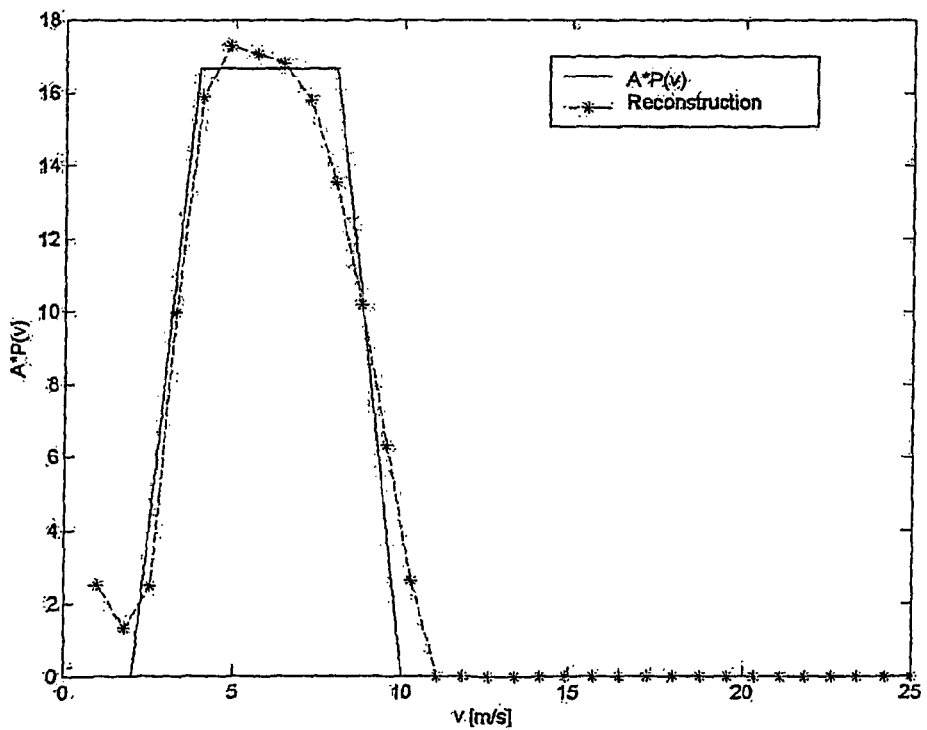

FIG. 24 represents the reconstruction of A·P(v); P(v) trapezoidal; J=100; tol=0.01.

Figure 25:
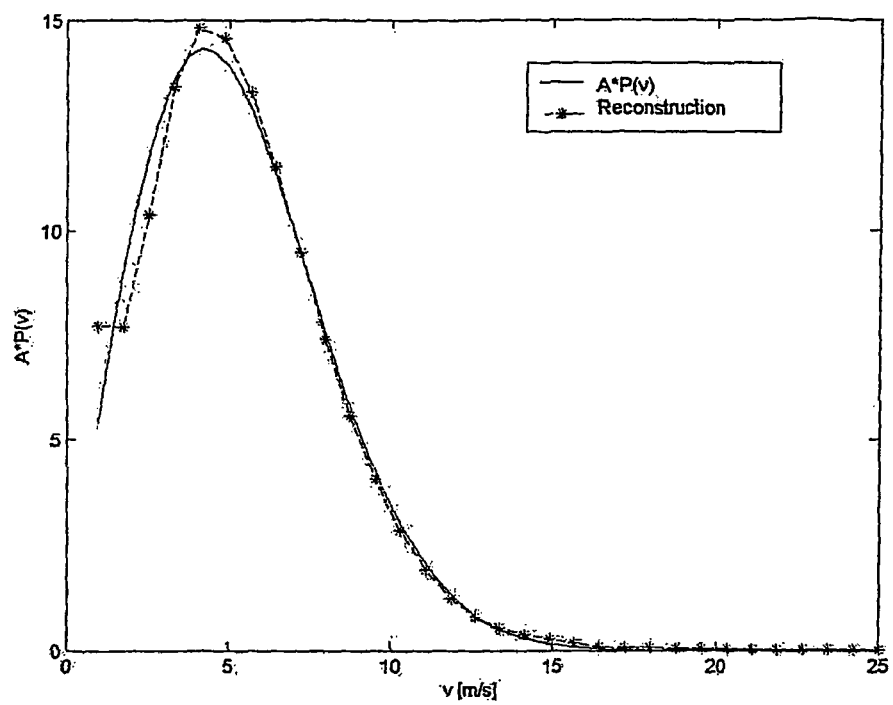

FIG. 25 represents the reconstruction of the Rayleigh P(v) defined by:

$$P(v) = \frac{2v}{b} e^{-(\frac{v}{b})^2},$$

where b=6. Namely this is a reconstruction of A·P(v); P(v) Rayleigh; J=50; tol=0.01.

Figure 26:
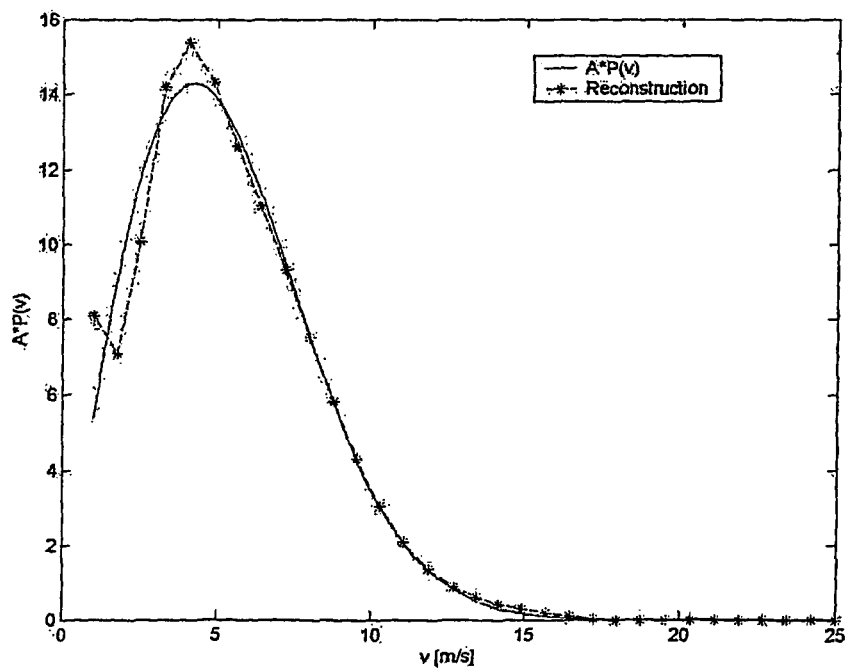

FIG. 26 is a reconstruction of A·P(v); P(v) Rayleigh; J=100; tol=0.01.

Figure 27:
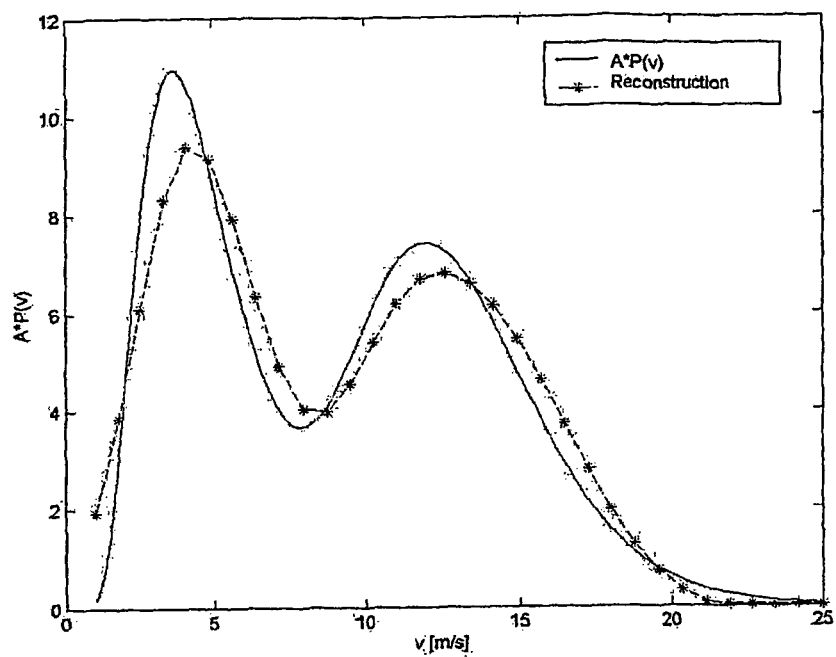

FIG. 27 is a reconstruction of the bimodal P(v) defined by:

$$P(v) = \frac{1}{2}lognormal(v, m_1, s_1) + \frac{1}{2}lognormal(v, m_2, s_2),$$

where $m_1 = 1.5, s_1 = 0.45, m_2 = 1.7 \cdot m_1, s_2 = \frac{s_1}{2}$.

This FIG. 27 is a reconstruction of A·P(v); P(v) bimodal; J=50; tol=0.01.

Figure 28:
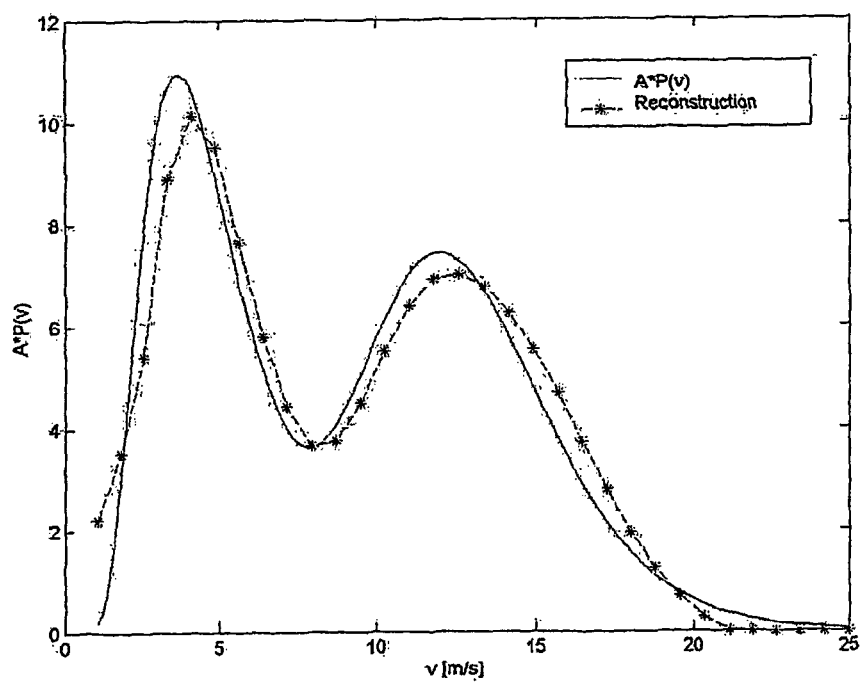

FIG. 28 is a reconstruction of A·P(v); P(v) bimodal; J=100; tol=0.01.

Figure 29:
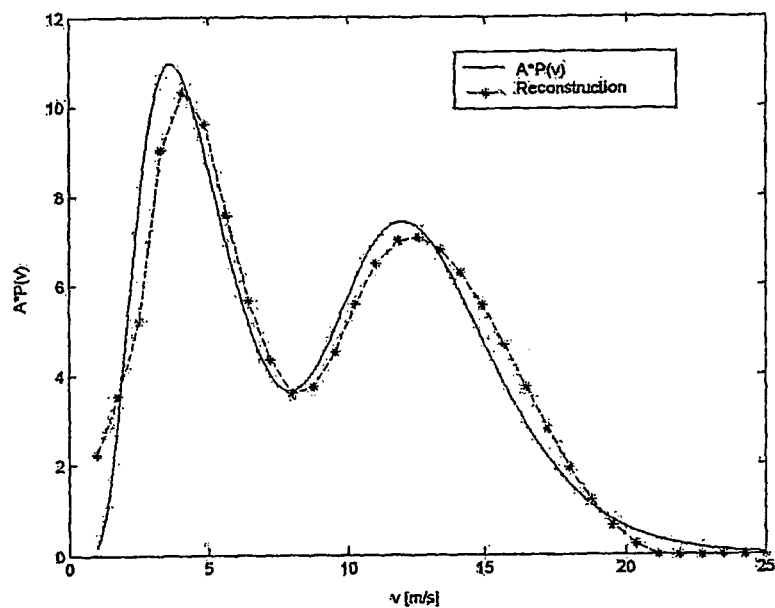

The reconstruction shown in FIG. 27 is not as good as that in FIG. 28; it has in fact been observed that, in the case of density probability distributions more complicated than a lognormal or a Gaussian distribution, the performance of the algorithm with J=50 can be improved, by using a smaller tolerance for the stopping criterion, for instance tol=0.001:

FIG. 29 is a reconstruction of A·P(v); P(v) bimodal; N=50; tol=0.001.

Figure 30:
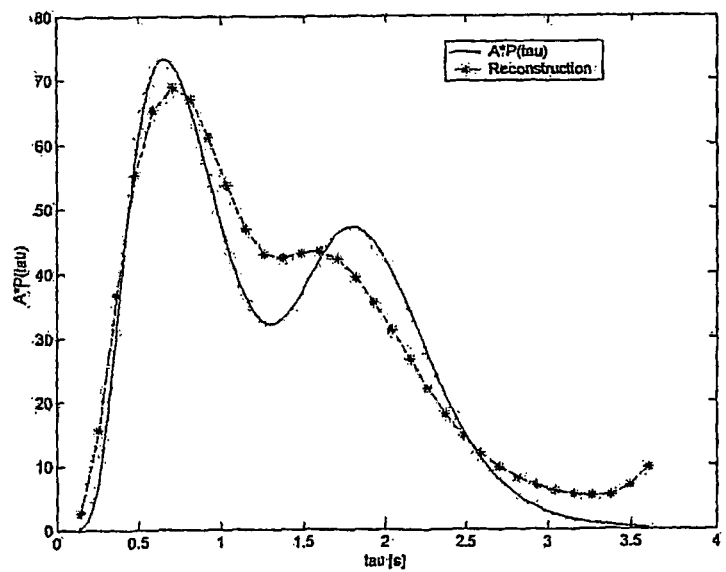

FIG. 30 is a reconstruction of the bimodal P(τ) defined by:

$$P(\tau) = \frac{3}{5}lognormal(\tau, m_1, s_1) + \frac{2}{5}lognormal(\tau, m_2, s_2),$$

where $m_1 = -0.2191, s_1 = 0.45, m_2 = -3 \cdot m_1, s_2 = s_1^2$.

Hence FIG. 30 is a reconstruction of A·P(τ); P(τ) bimodal; J=50; tol=0.01.

Figure 31:
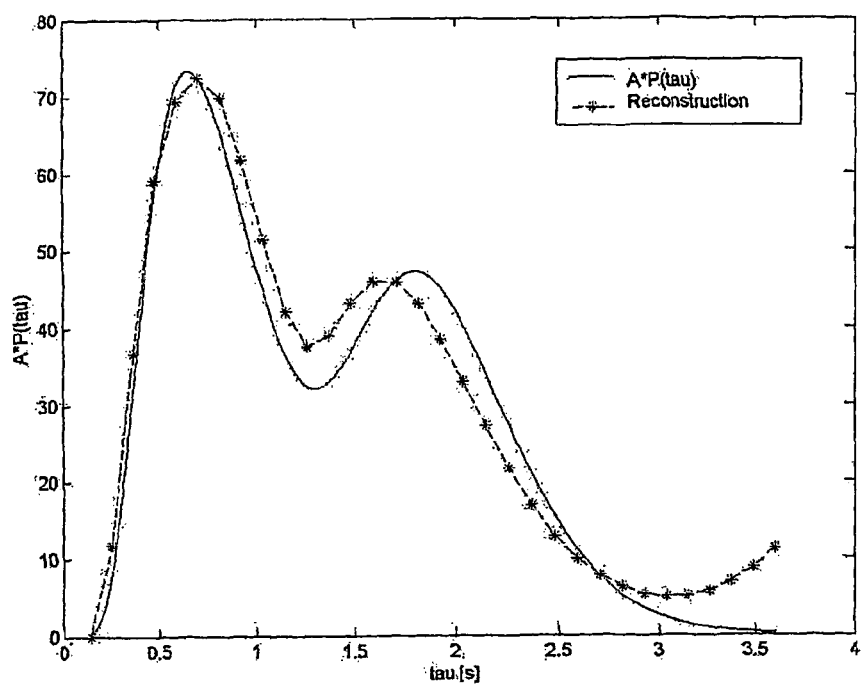

FIG. 31 is a reconstruction of A·P(τ); P(τ) bimodal; J=100; tol=0.01.

Figure 32:
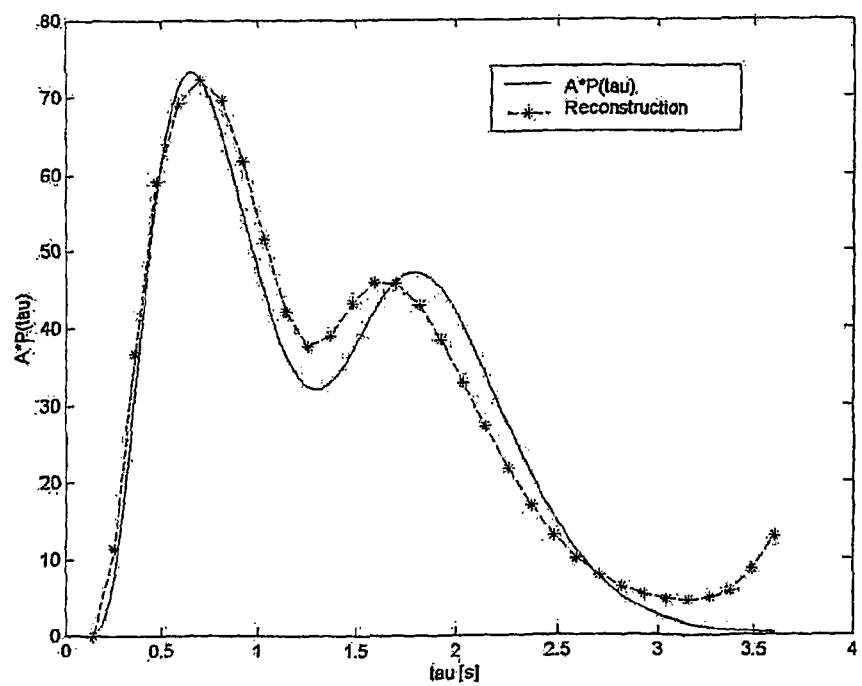

It can be observed that, in the specific example of FIG. 30, the algorithm with J=50 does not allow an accurate reconstruction of this bimodal distribution; as in the previous case, the performance of the algorithm can be improved by using a smaller tolerance for the stopping criterion as shown in FIG. 32 which is a reconstruction of A·P(τ); P(τ) bimodal; J=50; tol=0.001.

Figure 33:
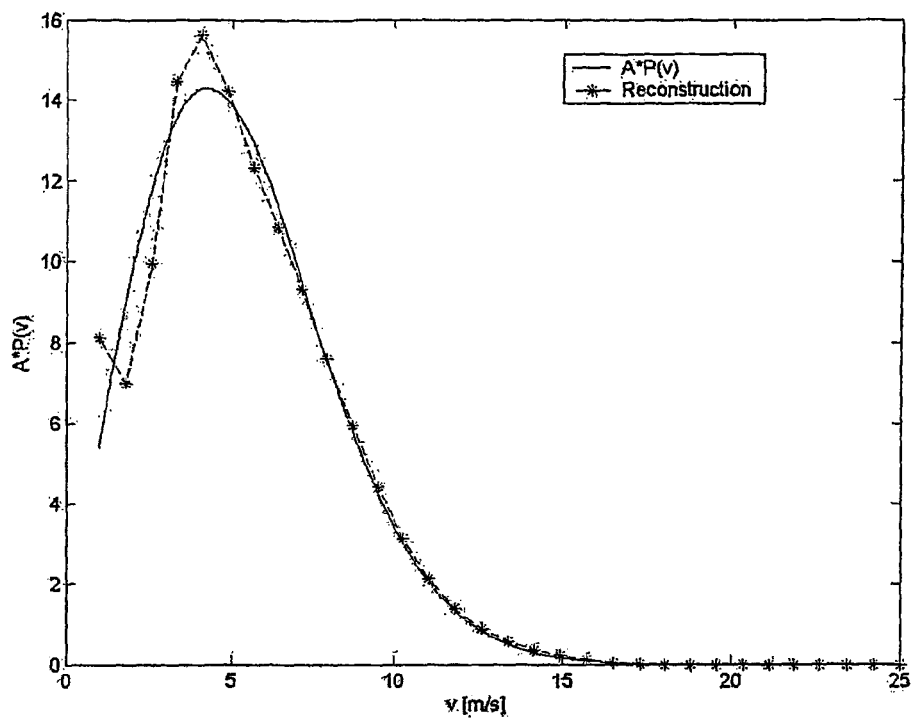

In this case the small tolerance has been very useful to improve the algorithm with J=50, but in general the issue is very delicate: using tol=0.001 can cause a loss of accuracy in cases of simple distributions, which are perfectly reconstructed with tol=0.01. For example, FIG. 25 illustrates a very good reconstruction of a Rayleigh distribution, obtained by using J=50 and tol=0.01. FIG. 33 shows the reconstruction of the same Rayleigh distribution, from the same E', obtained by using J=50 and tol=0.001.

Figure 34:
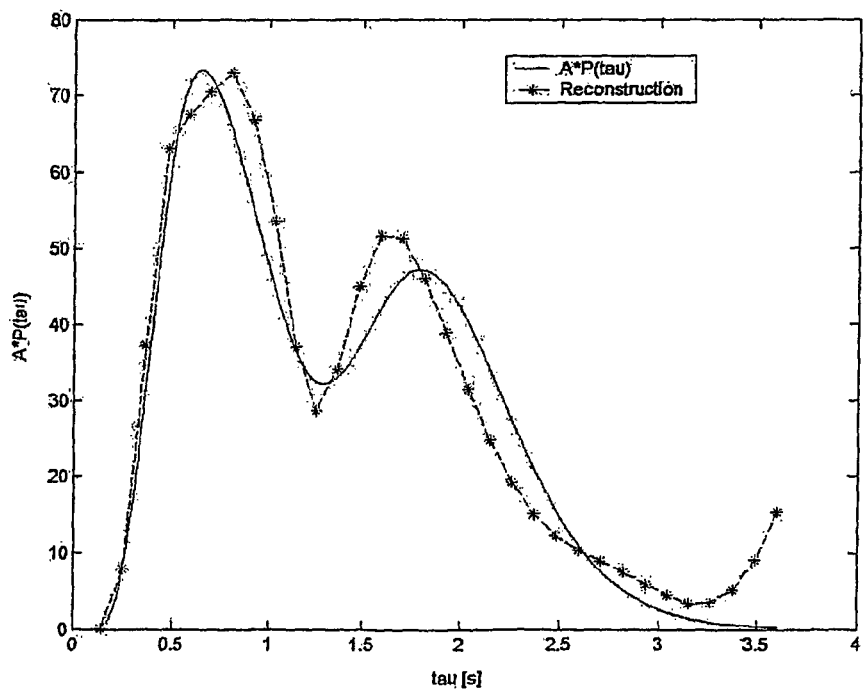

Differently from the case of the algorithm with J=50, if J=100 is used, the tolerance tol=0.001 is too small for any kind of distribution. A deterioration of the reconstruction accuracy also for bimodal distributions has in fact been observed. For example, for the bimodal of FIGS. 30-32, by using J=100 and tol=0.001, the reconstruction in FIG. 34 has been obtained, which is a reconstruction of A·P(τ); P(τ) bimodal; J=100; tol=0.001.

The objective to find a good approximation of P(ν) or, equivalently, P(τ), for any kind of distribution, without assuming any information about its form, has thus been achieved. It is thus possible to understand if there are anomalies in the region of interest, by comparing the reconstruction found with the lognormal distribution, characterizing healthy tissue.

Thanks to the above-mentioned final algorithm, good results in case of synthetic data with 10% of white noise are obtained.

In particular with these new methods it is possible to detect physiological anomalies by simply comparing the reconstruction found with the velocity distribution characterizing healthy tissue. With these new methods it is not necessary to differentiate the replenishment signal. In particular these new methods can provide very good results even for data with substantial noise.

Modifications

Many modifications of the described embodiments of the method and system are possible and the method and system can be used for determining many perfusion values or attributes, other than those described.

Moreover, the above-discussed multiple-step analysis, employing curve-fitting followed by neural network training, may be applied to perfusion functions other than the S-shape functions, obtained following a sequence of destruction frames under UCA infusion. An example is the case of a bolus injection of UCA arriving in a region under investigation. In the presence of multiple flow transit times, the expected echo-power bolus function E(t) can be considered as a sum of echo power functions $E_i(t)$, each determined by their flow transit times $\tau_i$. Such basic bolus functions $E_i(t)$, can be of the type:

$$E_i(t) = e^{\frac{t}{\tau_i}} e^{\frac{-t}{\tau_i}}.$$

Figure 35:
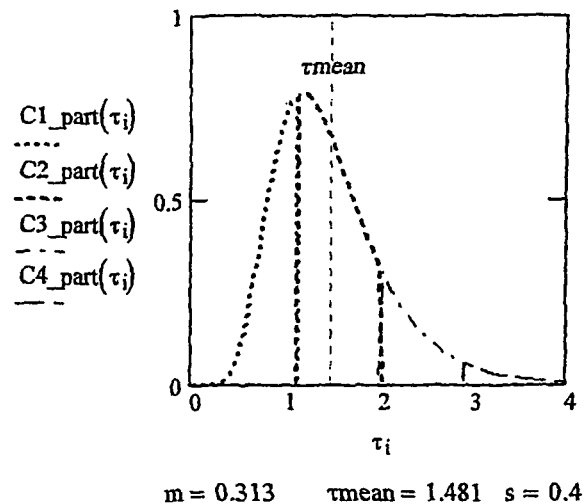
FIGS. 35 to 37 illustrate alternative applications of the one- or multi-step process.
Figure 36:
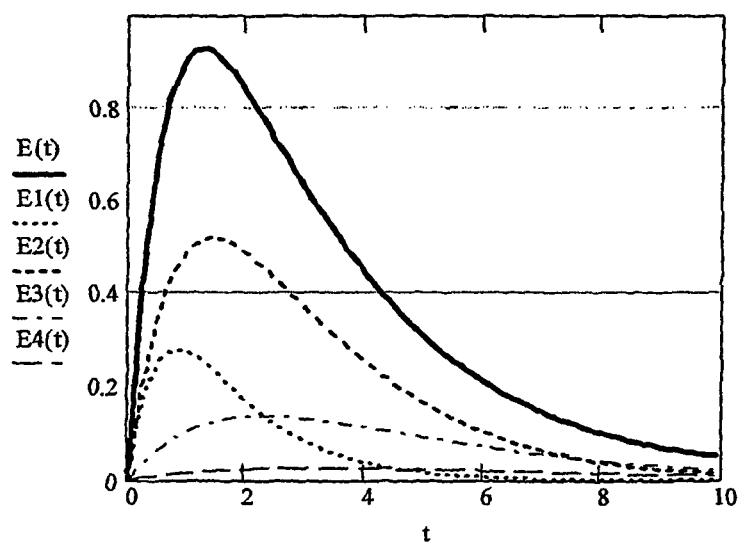

In the example illustrated in FIG. 35, a lognormal distribution of flow transit times $C(\tau_i)$ is considered, with m and s parameters equal to 0.313 and 0.4, respectively. Four partial sub-distributions of transit times are illustrated hereafter, referred to as $C1\_part(\tau_i)$ to $C4\_part(\tau_i)$, respectively. Considering the echo power function, E(t), resulting from the sum of four echo-power functions $E1\_part(t)$ to $E4\_part(t)$ determined by the partial sub-distributions, the analysis method may be applied to provide an estimate of the lognormal transit-time distribution C(τ), as illustrated in FIG. 36.

Figure 37:
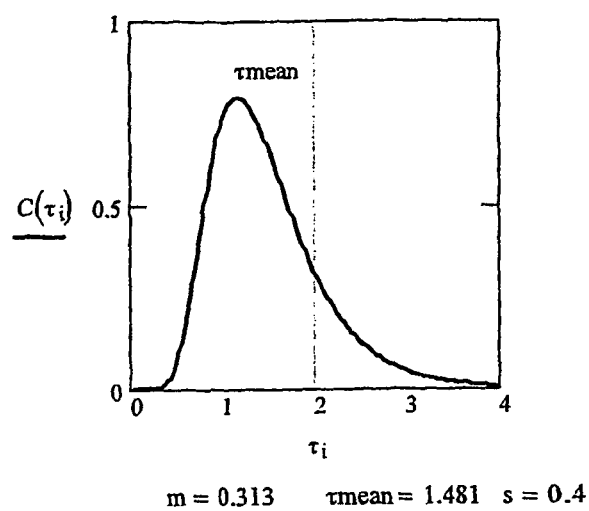

Analyzing the echo power function, according to the present invention, therefore allows the estimate of the original lognormal distribution as illustrated in FIG. 37.

Ultrasound Imaging System

Figure 38:
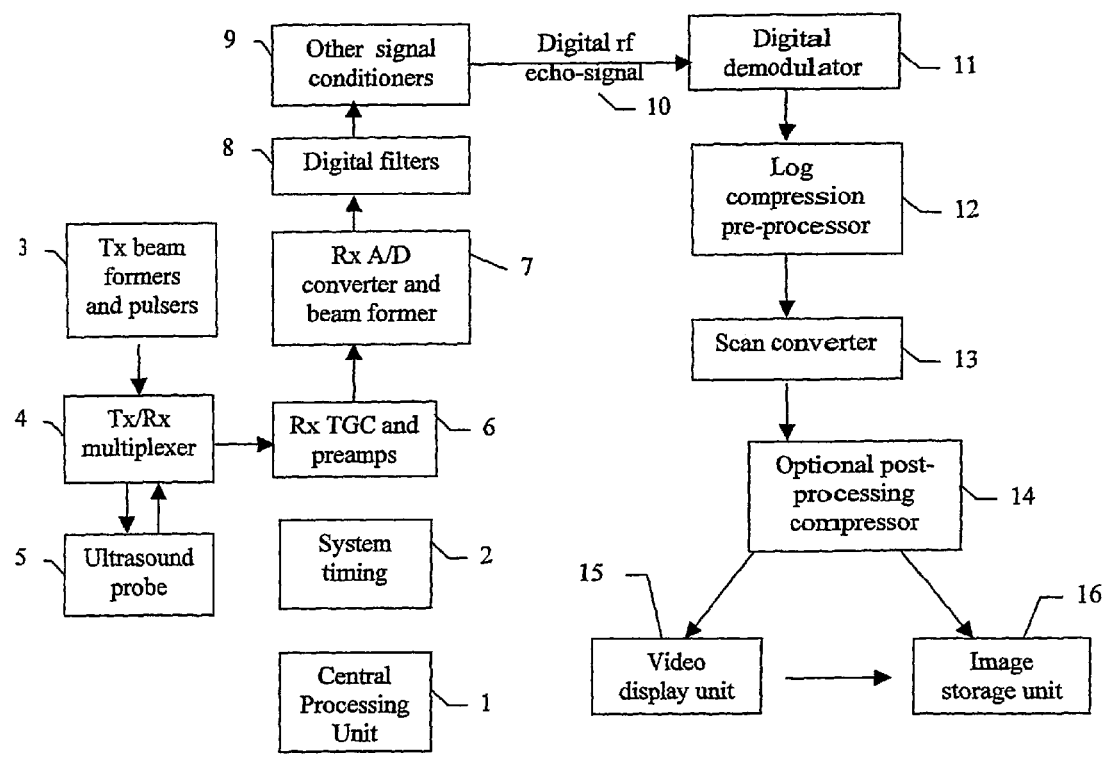
FIG. 38 is a block diagram showing the main elements of a typical medical ultrasound imaging system.

FIG. 38 shows a block diagram of the main elements of a typical medical ultrasound imaging system usable in the method according to the invention. Under the control of a Central Processing Unit 1 and central timing circuits 2, transmit beam formers and pulsers 3 are used to apply, through appropriate Tx/Rx (transmit/receive) multiplexers 4, excitation signals to a multi-element ultrasound probe 5. Upon ultrasound reflection within the propagating medium, echo signals are processed through pre-amplifiers and preliminary time-gain compensation (TGC) 6. Typically, these received signals are then converted from analog voltages to digital values by an A/D converter, and combined into focused receive signals through a receive beam former 7. By processing through digital filters 8 (e.g. band-pass filters), and other signal conditioners 9 (e.g. post-beamforming TGC), the digital radiofrequency (rf) signals 10 are processed by a demodulator 11 to generate signals proportional the echo-envelope amplitude, and further nonlinearly processed (e.g. by a log compression pre-processor 12) before being written to a scan-converter 13, to account for the probe geometry and beam scanning sequences. The scan converted signals are optionally compressed again (by a post-processor 14), then converted into a video-standard signal. The video signal can then be displayed on a video display unit 15 and/or stored on a storage unit 16, either in analog form (in this case the storage unit 16 will be a video-recording equipment) or in digital form, e.g. as computer files (in this case the storage unit 16 can be a hard-disk). The so-obtained images are then processed according to the invention, as explained hereinafter.

When using such an ultrasound imaging system to implement the method according to the invention, the signals used for the analysis of the reperfusion kinetics according to the invention are preferably obtained from a contrast-specific detection scheme, such as those exploiting the nonlinear acoustic response of microvesicles, in amplitude-sensitive modes (such as harmonic B-mode, pulse-inversion or power-modulation multipulse modes, or other coded excitation or demodulation single-pulse or multipulse modes). Alternatively, the signals used for the analysis of the reperfusion kinetics can be obtained from contrast-specific detection schemes in Doppler modes (such as harmonic power Doppler, decorrelation imaging, or other modes exploiting the changes in responses occurring in response to successive excitation pulses, due to changes in position or in acoustic responses of the microvesicles).

System/Method for Flow-Velocity Estimates

Figure 39:
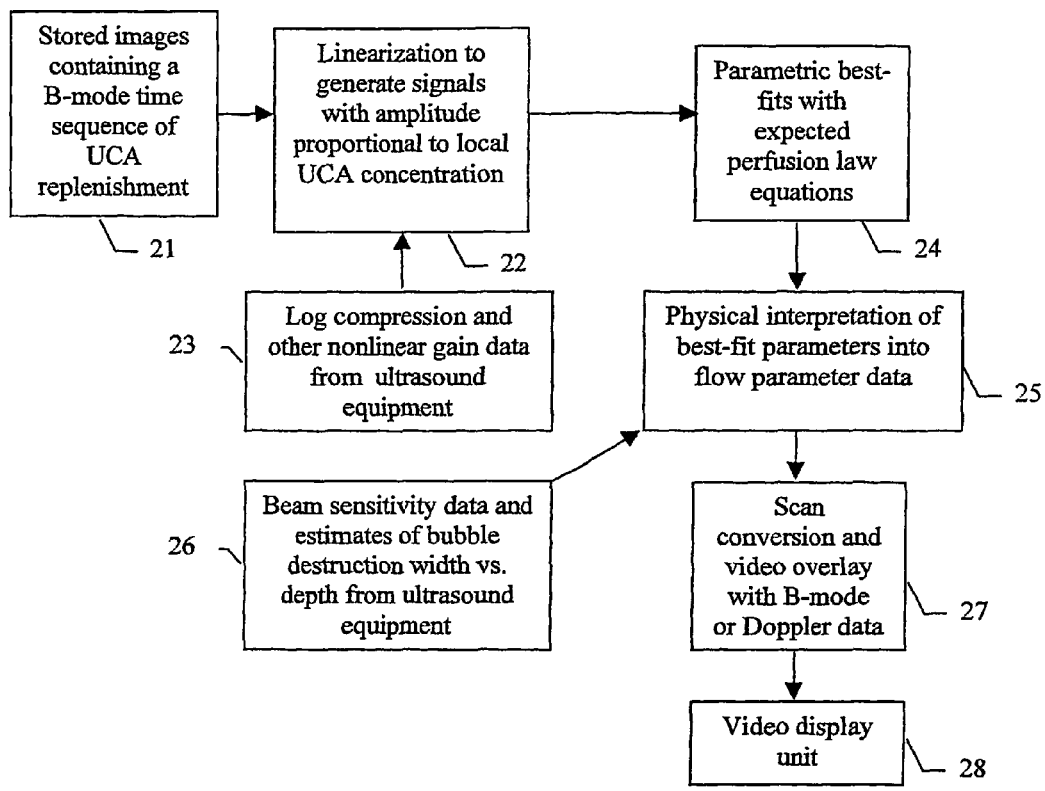
FIG. 39 is a block diagram showing the main functional elements of the flow estimation method/system in one particular example of parametric flow imaging according to the invention.

FIG. 39 is a block diagram showing the main functional elements of a system according to the invention for carrying out the flow estimation method in one particular example of parametric flow imaging. Starting from computer files 21 (e.g. from digital file storage 16 of FIG. 38) containing a sequence of B-mode images including the replenishment of UCA following destruction, image values are processed by appropriate linearization 22 to produce data proportional to local UCA concentration, based on log-compression or other nonlinear gain data 23 particular to the ultrasound equipment used. The time-sequence data are then adjusted by best-fit methods 24, according to the present invention, to a parametric equation describing the expected perfusion law, as set out above. The physical interpretation 25 of these parameters requires input data 26 from the ultrasound equipment, such as the Tx/Rx beam sensitivity data and the estimates of the thickness of the bubble-destruction zone D. The best-fit parameters allow the computation of mean flow-velocity data, mean transit-time distribution estimates, or other flow characteristics, which can then be mapped, by known gray-scale or pseudo-color coding, in a scan-conversion memory 27 and optionally overlaid with B-mode or 2-dimensional Doppler data, and displayed on a video display unit 28 or stored in digital or analog form (not shown).

The functional elements of the system according to the invention can be stored on a program that is operable when loaded in a computer (the CPU 1, or a computer associated with units 11-15) for, automatically or under manual control, relating the signal proportional to the local agent concentration during reperfusion to a corresponding function of time with S-shape characteristics. The mathematical functions used can for example be implemented using the MATLAB® Curve Fitting Toolbox (MathWorks, Natick, Mass., USA). This program preferably further embodies means for processing the amplitudes of the recorded echo signals to make said signals proportional to the local concentration of microvesicles, and is operable when loaded in a computer of the system for automatically or under manual control effecting said processing before the processed signals are adjusted or related to the S-shape parametric function. The program also preferably includes the means for, automatically or under manual control, making a correspondence between at least one value of at least one parameter of the function with S-shape characteristics and at least one local tissue perfusion value or attribute. This fitting can for example be computed using the afore-mentioned Trust Region method. Both of these principal functions can be implemented automatically or semi-automatically, with appropriate user interfaces allowing control by the user.

Estimation of the tissue perfusion values within chosen areas of interest can be determined by the user performing the investigation or by automatic means, based on automatic border delineation or other anatomical organ features, incorporated in the system program. When the perfusion values are estimated within individual two-dimensional picture elements, or pixels, these can be displayed on a viewing monitor (15) in the form of parametric images, where the pixel grayscale intensities or color rendering is coded according to the values of individual locally-estimated parameters, or combinations thereof. The system program can also estimate perfusion values within groups of two-dimensional picture elements, or pixels, these groups being determined by the local imaging resolution in such a way that substantially one value only of each parameter is obtained for each group of pixels. Typically, when the perfusion values are estimated within groups of pixels, these groups can be substantially determined (automatically) by the local speckle pattern of the echographic instrument. The sizes of groups of pixels can be determined from a two-dimensional spatial Fourier analysis of the local echographic image, and whose extents are inversely proportional to the maximum significant spatial frequencies present locally, all calculated automatically by the system program, or under user control. The program can also estimate the flow parameters from the time lapse between the last destruction ultrasound pulses and the instant when the S-shape function reaches an amplitude equivalent to an agent concentration one half of the concentration value present immediately before applying the destruction ultrasound pulses.

The system program can also compute the mean local blood velocity as expressed by the ratio of one-half the thickness of the slice where the microvesicles are destroyed divided by the time to half-maximum concentration. For this purpose, it can also provide an approximation of the value of the thickness of the slice where the microvesicles are destroyed from the transmit beam elevation width, in a direction perpendicular to the imaging plane.

The system program can compute the steady-state agent concentration level as the asymptotic value of the S-shape function fit for large time values following the destruction pulses, or this concentration level can be taken as a value immediately preceding the destruction pulses.

The system program can compute the S-shape function as: a cumulative normal probability distribution function; or as a sigmoid function; or as a polynomial approximation of a cumulative normal probability distribution function; or as a parametric expression including limited expansion of a polynomial form; or as a parametric expression of a cumulative lognormal probability distribution function, all as described in greater detail above. In one embodiment, it computes the S-shape function as a parametric expression of a sum or integral of cumulative normal probability distribution functions, weighted by a lognormal probability distribution of flow velocities or transit times, and whose best-fit parameter values represent physical quantities of organ perfusion, such as flow velocity or transit time, as well as their mean, variance and skewness.

Flow velocity values can be estimated using a smoothed or filtered version of the reperfusion function to estimate the time to half steady-state echo-power amplitude.

The signals proportional to local concentration are advantageously processed through a low-pass filter or other smoothing function before being adjusted by the parametric fitting function. Instead of being linearized, the signals proportional to local concentration can be adjusted with the parametric fitting functions modified by nonlinear functions of the same nature as those being applied in the echographic instrument.

As described in detail above with reference to FIG. 9*a-d*, the echo-power data can be analyzed by the wavelet decomposition method to estimate the distribution of contributions at different flow transit times or velocities. For this, the signals proportional to local concentration are preferably first low-pass filtered or smoothed before being analyzed by the wavelet decomposition method; they can also be differentiated twice before being analyzed by the wavelet decomposition method. In the wavelet method, a mother wavelet used for the decomposition is for example the second time derivative of the cumulative normal distribution function used to describe the reperfusion function for a single flow value.

In addition or in alternative, the echo-power data is analyzed by a one step or a multiple step process to estimate the distribution of contributions at different flow transit times or velocities. In the first step a first set of flow transit times or velocities is selected and a first estimate is made by a best fit of a linear combination of a plurality of S-shaped functions with the echo power data. A second estimate is then made for a second set of flow transit times or velocities, using the first estimate as a basis for defining the second set. The second estimate can then be used to provide an initial set of values for making a third estimate.

The second estimate can for example be made using cubic spline extrapolation whereas the third estimate is advantageously made using a neural network analysis; in this case, the bias values and each negative weight of the neural networks are preferably reset to zero periodically (for example, every 50-100 iterations of the adjusting thereof). The first estimate can be made using a relatively small number of S-shaped functions usually at most 16 and preferably at most 8 S-shaped functions. The second estimate can then be made using a greater number of flow transit times or velocities, for example using a set of at least 8 and preferably at least 16 flow transit times or velocities.

The signal(s) proportional to local concentration can also be derived from radiofrequency echo signals (i.e. at 10 in FIG. 38), for example by squaring the demodulated echo signals. Alternatively, the signal(s) proportional to local concentration is/are derived from video echo signals, following logarithmic compression (at 14 in FIG. 38), by applying an inverse logarithmic compression inversing the effects of logarithmic compression, and followed by squaring these signals. In one embodiment, the signal(s) proportional to local concentration is/are obtained from a contrast-specific detection scheme exploiting the nonlinear acoustic response of microvesicles in amplitude-sensitive modes (such as harmonic B-mode, pulse-inversion or power-modulation multipulse modes, or other coded excitation or demodulation single-pulse or multipulse modes).

The system program can be provided in one or more modules loadable into one or more computers of the imaging system, allowing automatic or semi-automatic implementation of the inventive method under the control of the user. All mathematical functions for carrying out the described process steps can be automated.

The program is typically provided on CD-ROM, DVD, or any other computer readable medium; alternatively, the program is pre-loaded onto the hard-disk, is sent to the computer through a network, is broadcast, or more generally is provided in any other form directly loadable into the working memory of the computer. However, the method according to the present invention leads itself to be carried out with a hardware structure (for example, integrated in a chip of semiconductor material), or with a combination of software and hardware.

Moreover, it should be noted that the program described-above is suitable to be put on the market even as a stand-alone product, in order to be used on existing ultrasound imaging systems; for example, the program can be used on a computer that is integrated in the system or on a external computer that receives the sequence of echo signals provided by a separate scanner (such as through a removable disk, a communication line or a wireless connection).

Example

Figure 40A:
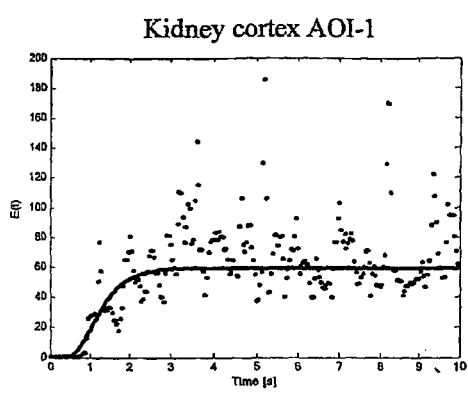
FIGS. 40a and 40b show experimental results of replenishment functions for two Areas of Interest, respectively in normally perfused and hypo-perfused areas of a kidney cortex.
Figure 40B:
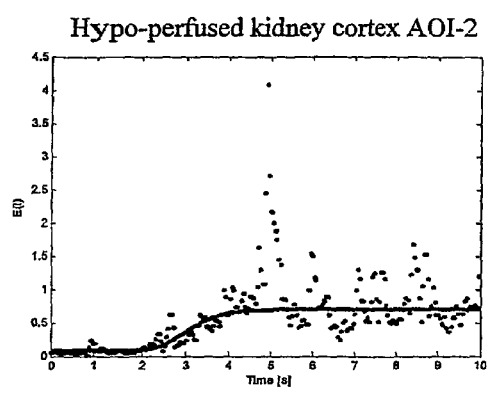

To illustrate the applicability of the disclosed invention to the in-vivo situation, an artificial occlusion (stenosis) was created in a kidney of a minipig, using an inflatable intra-arterial balloon. The contrast agent used was SONOVUE® (Bracco Imaging S.p.A.: an aqueous suspension of stabilized SF6 microbubbles sized between 1 and 10 µm, and between 2 and $5 \times 10^8$ microbubbles per mL), administered at a constant infusion rate of 1 mL/min intravenously. The ultrasound-imaging equipment used was an HDI-5000 from ATL/Philips (Bothell, Wash.), using a C5-2 convex probe in pulse-inversion contrast-specific B-mode imaging. Sequences of UCA destruction/replenishment images were recorded and transferred to a computer for the reperfusion analysis. Two areas of interest (AOI) were drawn in the kidney cortex, using a videodensitometry program allowing grayscale linearization. The first one, AOI-1, was drawn in the normally-perfused kidney cortex, whereas the other, AOI-2, was drawn within the hypo-perfused area of the cortex. The linearized videodensitometric data points for AOI-1 and AOI-2 are illustrated, as a function of time, in FIG. 40a and FIG. 40b, respectively, for the first 10 seconds following the application of bubble-destruction frames. The best-fit logperf energy functions, E(t), are shown as solid lines on the corresponding graphs. The most relevant best-fit parameters found for these two AOIs are: A=59.5 and A=0.62, τ=1.25 s and τ=3.1 s, for AOI-1 and AOI-2, respectively. With D values of 6 and 8 mm for the two regions, the determined mean transverse flow velocities, $v_y$, are 2.4 mm/s and 0.97 mm/s, respectively. Relative volume flows are found by the product of A and $v_y$, i.e. values of 142.8 and 0.6 for AOI-1 and AOI-2, respectively, thus indicating very large flow differences between the two cortical areas.

Naturally, in order to satisfy local and specific requirements, a person skilled in the art may apply to the solution described above many modifications and alterations all of which, however, are included within the scope of protection of the invention as defined by the following claims.

The invention claimed is:

1. A method of non-invasive quantification of perfusion in a tissue of a live subject, comprising:
   receiving with a computing device a sequence of echo signals indicative of a replenishment of an imaging contrast agent in said tissue following a destruction of a significant portion of the imaging contrast agent;
   associating with the computing device a parametric S-shape function of time with the echo signals, said S-shape function including an initial portion with a constant initial value and a zero first derivative over a non-zero period of time following the destruction of the imaging contrast agent, a final portion with a constant final value and a zero first derivative, and a central portion between the initial portion and the final portion wherein said S-shape function changes monotonically from the initial value to the final value; and
   making a correspondence with the computing device between at least one value of at least one parameter of said S-shape function and at least one local tissue perfusion flow value or flow attribute.

2. The method according to claim 1, wherein said contrast agent includes microvesicles having the capacity to reflect acoustic energy, said sequence of echo signals being obtained by:
   administering said contrast agent to the live subject;
   applying an ultrasound pulse in an imaging plane of an ultrasound imaging apparatus, at an acoustic pressure sufficiently high to result in the destruction of a significant portion of the microvesicles present within that plane;
   applying a sequence of further ultrasound pulses in said imaging plane, said further ultrasound pulses having an acoustic pressure sufficiently low to preserve a major portion of the microvesicles; and
   repeating applying the sequence of further ultrasound pulses at predetermined subsequent instants, and recording the echo signals originating from said plane by the further ultrasound pulses to monitor the replenishment of microvesicles within the imaging plane at said subsequent instants.

3. The method according to claim 1, further comprising, before associating the S-shape function:
   processing said echo signals to make the echo signals proportional to a local concentration of the microvesicles thereby producing processed echo signals that are in proportion to a concentration of the contrast agent at any location within the imaging plane.

4. The method according to claim 3, wherein the echo signals are obtained as a two dimensional image associated to image elements proportional to an amplitude of said echo signal, and said processing includes linearization of said echo signals.

5. The method according to claim 3, wherein the echo signals have an amplitude proportional to an ultrasound echo amplitude and said processing includes linearization of said echo signals.

6. The method according to claim 5, wherein the echo signals are radio-frequency signals or demodulated radio-frequency signals.

7. The method according to claim 1, wherein the tissue perfusion value or attribute is estimated within a chosen area of interest.

8. The method according to claim 1, wherein the perfusion value or attribute is estimated within individual two-dimensional image elements and then displayed on a viewing monitor in the form of parametric images as pixel grayscale intensities or color rendering, where the pixel grayscale intensities or color rendering is coded according to the values of the individual locally-estimated parameters, or combinations thereof.

9. The method according to claim 1, wherein the perfusion value or attribute is estimated within groups of two-dimensional image elements, said groups being determined by a local imaging resolution in such a way that substantially one value only of each parameter is obtained for each group of image elements.

10. The method according to claim 1, wherein the perfusion value or attribute is estimated within groups of image elements, said groups of image elements having sizes that are substantially determined by a local speckle pattern of an echographic instrument of the ultrasound apparatus.

11. The method according to claim 10, wherein the sizes of said groups of image elements are determined from a two-dimensional spatial Fourier analysis of a local echographic image, and are inversely proportional to a maximum significant spatial frequencies present locally.

12. The method according to claim 1, wherein said correspondence is made with at least one perfusion value selected among the following: perfusion mean transit time, perfusion mean velocity, perfusion mean flow and perfusion volume.

13. The method according to claim 1, wherein the S-shape function is based on a plurality of elementary perfusion functions with said S-shape, each one for a corresponding value of at least one flow parameter, the elementary perfusion functions being weighted according to a probability density distribution of the at least one flow parameter, the at least one parameter of said S-shape function being a statistic indicator of the probability density distribution of the at least one flow parameter.

14. The method of claim 13, wherein the probability density distribution is a lognormal probability distribution.

15. The method according to claim 1, wherein the perfusion flow velocity is estimated from a time lapse between the ultrasound pulse and an instant when the S-shape function reaches a value equivalent to a concentration of the contrast agent one half of the concentration present immediately before applying the ultrasound pulse.

16. The method according to claim 15 wherein said contrast agent includes microvesicles having the capacity to reflect acoustic energy, said sequence of echo signals being obtained by:
administering said contrast agent to the live subject;
applying an ultrasound pulse in an imaging plane of an ultrasound imaging apparatus, at an acoustic pressure sufficiently high to result in the destruction of a significant portion of the microvesicles present within that plane;
applying a sequence of further ultrasound pulses in said imaging plane, said further ultrasound pulses having an acoustic pressure sufficiently low to preserve a major portion of the microvesicles; and
repeating applying the sequence of further ultrasound pulses at predetermined subsequent instants, and recording the echo signals originating from said plane by the further ultrasound pulses to monitor the replenishment of microvesicles within the imaging plane at said subsequent instants; and
wherein said perfusion value is a mean local blood velocity which is expressed as the ratio between one-half a thickness of a slice where the microvesicles are destroyed and a time to half-maximum concentration.

17. The method according to claim 16, wherein the thickness of the slice where the microvesicles are destroyed is approximated by the value of a width, in a direction perpendicular to the imaging plane, of the applied ultrasound pulse.

18. The method according to claim 1, wherein the imaging contrast agent is suitable to be administered intravenously as a continuous infusion.

19. The method according to claim 1, wherein the imaging contrast agent is administered intravenously as a bolus in such a way as to provide a period of several seconds with a local agent concentration supply of essentially constant value to the imaged area until the local concentration reaches at least one-half the concentration existing immediately prior to applying an ultrasound pulse.

20. The method according to claim 1, wherein the S-shape function is a cumulative normal probability distribution function, a sigmoid function or a polynomial approximation of a cumulative normal probability distribution function.

21. The method according to claim 1, wherein the S-shape function is a parametric expression including limited expansion of a polynomial form or a parametric expression of a cumulative lognormal probability distribution function.

22. The method according to claim 1, wherein the echo signals are processed through a smoothing function before associating the S-shape function.

23. The method according to claim 1, wherein said echo signals are analyzed by a wavelet decomposition method to make a first flow-contribution-distribution estimate at different flow transit times or velocities.

24. The method according to claim 23, wherein an echo signal proportional to local contrast agent concentration is differentiated twice before being analyzed by the wavelet decomposition method.

25. The method according to claim 24, wherein a mother wavelet used for the decomposition is the second time derivative of a cumulative normal distribution function used to describe the S-shape function for a single flow value.

26. The method according to claim 1, wherein the echo signals are analyzed to make a first flow-contribution-distribution estimate at different flow transit times or velocities, the analysis including:
selecting a first set of flow transit times or velocities; and
making the first flow-contribution-distribution estimate by a best fit of a linear combination of a plurality of S-shaped functions with the echo signals.

27. The method according to claim 26 wherein said first set of flow transit times or velocities is obtained from a linear combination of from 4 to 16 S-shape functions.

28. The method according to claim 26, wherein the analysis further includes:
making a second flow-contribution-distribution estimate to define a second set of flow transit times or velocities, using said first flow-contribution-distribution estimate as a basis for defining said second set.

29. The method according to claim 28 wherein said second set of flow transit times or velocities is obtained from a linear combination of from 8 to 64 S-shape functions.

30. The method according to claim 28 wherein the second flow-contribution-distribution estimate is used for making a third flow-contribution-distribution estimate.

31. The method according to claim 28 wherein the second flow-contribution-distribution estimate is made using cubic spline extrapolation.

32. The method according to claim 28 wherein the third flow-contribution-distribution estimate is made using a neural network analysis.

33. The method according to claim 32, wherein the neural network is defined by a plurality of weights for the flow transit times or velocities and a plurality of bias values for the weighted flow transit times or velocities, the third flow-contribution-distribution estimate including:
 iteratively adjusting the bias values and the weights, and
 periodically resetting the bias values and each negative weight to zero.

34. The method according to claim 33, wherein the resetting is performed with a periodicity equal to a number of iterations between 10 and 200.

35. The method of claim 26 wherein the first flow-contribution-distribution estimate is made using at most 8 S-shaped functions.

36. The method of claim 35 wherein the second flow-contribution-distribution estimate is made using a set of at least 16 flow transit times or velocities.

37. The method of claim 1, wherein the S-shape function comprises at least one approximately zero second derivative in the central portion.

38. The method of claim 1,
 wherein the at least one local tissue perfusion flow value or flow attribute is blood flow pattern; and
 wherein the S-shape function is defined by an unknown sum of individual perf functions without any assumption about distribution of flow transit times.

39. The method of claim 1,
 wherein the at least one local tissue perfusion flow value or flow attribute is flow distribution variance and/or flow skewness; and
 wherein the S-shaped function is defined as a perf function or a linear combination of perf functions weighted by lognormal distribution of flow velocities.

40. The method of claim 1, wherein the central portion of the S-shape function has at least one zero second derivative.

41. A method of non-invasive quantification of perfusion in a tissue of a live subject, comprising:
 obtaining with a computing device a sequence of echo signals indicative of a replenishment of an imaging contrast agent in said tissue,
 associating with the computing device a parametric S-shape function of time with the echo signals, said S-shape function including an initial portion with a substantially constant initial value over a non-zero period of time, a final portion with a substantially constant final value, and a central portion between the initial portion and the final portion wherein said S-shape function changes monotonically from the initial value to the final value; and
 making a correspondence with the computing device between at least one value of at least one parameter of said S-shape function and at least one local tissue perfusion flow value or flow attribute,
 wherein the S-shape function is a parametric expression of a sum or integral of cumulative normal probability distribution functions, weighted by a lognormal probability distribution of flow velocities or transit times, the S-shape function having best-fit parameter values that represent physical quantities of organ perfusion; or
 wherein the S-shape function is a cumulative normal probability distribution function, a sigmoid function or a polynomial approximation of a cumulative normal probability distribution function.

42. A non-transitory computer readable medium comprising instructions, that when executed by a processor, carry out the steps of:
 associating a parametric S-shape function of time with received echo signals, said S-shape function including an initial portion with a constant initial value and a zero first derivative over a non-zero period of time following a destruction of at least a significant portion of an imaging contrast agent, a final portion with a constant final value and a zero first derivative, and a central portion between the initial portion and the final portion wherein said S-shape function changes monotonically from the initial value to the final value; and
 making a correspondence between at least one value of at least one parameter of said S-shape function and at least one local tissue perfusion flow value or flow attribute.

43. The method of claim 42, wherein the central portion of the S-shape function has at least one zero second derivative.

44. A system of non-invasive quantification of perfusion in a tissue of a live subject, the system comprising:
 means for providing a sequence of echo signals indicative of a replenishment of an imaging contrast agent in said tissue;
 means for associating a parametric S-shape function of time with the echo signals, said S-shape function including an initial flat portion with a constant initial value and a zero first derivative over a non-zero period of time, a final portion with a constant final value and a zero first derivative, and a central portion between the initial portion and the final portion wherein said S-shape function changes monotonically from the initial value to the final value; and
 means for making a correspondence between at least one value of at least one parameter of said S-shape function and at least one local tissue perfusion flow value or flow attribute.

45. The system according to claim 44, wherein said contrast agent includes microvesicles having the capacity to reflect acoustic energy, the means for providing the sequence of echo signals including means for applying an ultrasound pulse in an imaging plane of an ultrasound imaging apparatus, at an acoustic pressure sufficiently high to result in the destruction of a significant portion of the microvesicles present within that plane, means for applying a sequence of further ultrasound pulses in said imaging plane, said further ultrasound pulses having an acoustic pressure sufficiently low to preserve a major portion of the microvesicles, and means for recording the echo signals originating from said plane by the further ultrasound pulses at predetermined subsequence instants to monitor the replenishment of microvesicles within the imaging plane at said subsequent instants.

46. The system according to claim 44, further including means for processing said echo signals, before associating the S-shape function, to make the echo signals proportional to a local concentration of the microvesicles thereby producing processed echo signals that are in proportion to a concentration of the contrast agent at any location within the imaging plane.

47. The method of claim 44, wherein the central portion of the S-shape function has at least one zero second derivative.

* * * * *